US008679749B2

(12) United States Patent
Glick et al.

(10) Patent No.: US 8,679,749 B2
(45) Date of Patent: Mar. 25, 2014

(54) RED FLUORESCENT PROTEINS WITH ENHANCED BACTERIAL EXPRESSION, INCREASED BRIGHTNESS AND REDUCED AGGREGATION

(75) Inventors: Benjamin S. Glick, Chicago, IL (US); Daniel E. Strongin, Seattle, WA (US); Robert Keenan, Chicago, IL (US); Rita L. Strack, Towson, MD (US); Dibyendu Bhattacharyya, Oak Park, IL (US)

(73) Assignee: The University of Chicago, Chicago, IL (US)

( * ) Notice: Subject to any disclaimer, the term of this patent is extended or adjusted under 35 U.S.C. 154(b) by 565 days.

(21) Appl. No.: 12/740,019

(22) PCT Filed: Nov. 3, 2008

(86) PCT No.: PCT/US2008/082264
§ 371 (c)(1),
(2), (4) Date: Sep. 28, 2010

(87) PCT Pub. No.: WO2009/059305
PCT Pub. Date: May 7, 2009

(65) Prior Publication Data
US 2011/0020784 A1    Jan. 27, 2011

Related U.S. Application Data

(60) Provisional application No. 60/984,642, filed on Nov. 1, 2007.

(51) Int. Cl.
*C12N 15/12* (2006.01)
*C07K 14/435* (2006.01)

(52) U.S. Cl.
USPC ...... 435/6.1; 435/252.3; 435/320.1; 435/325; 435/69.1; 435/69.7; 536/23.4; 536/23.5

(58) Field of Classification Search
None
See application file for complete search history.

(56) References Cited

U.S. PATENT DOCUMENTS

| | | | |
|---|---|---|---|
| 972,628 | A | 10/1910 | Pease et al. |
| 4,302,536 | A | 11/1981 | Longenecker |
| RE30,985 | E | 6/1982 | Cartaya |
| 4,399,216 | A | 8/1983 | Axel et al. |
| 4,551,433 | A | 11/1985 | DeBoer |
| 4,560,655 | A | 12/1985 | Baker |
| 4,657,866 | A | 4/1987 | Kumar |
| 4,683,195 | A | 7/1987 | Mullis et al. |
| 4,683,202 | A | 7/1987 | Mullis |
| 4,745,051 | A | 5/1988 | Smith et al. |
| 4,767,704 | A | 8/1988 | Cleveland et al. |
| 4,837,148 | A | 6/1989 | Cregg |
| 4,927,762 | A | 5/1990 | Darfler |
| 4,929,555 | A | 5/1990 | Cregg et al. |
| 5,182,202 | A | 1/1993 | Kajiyama et al. |
| 5,221,623 | A | 6/1993 | Legocki et al. |
| 5,229,285 | A | 7/1993 | Kajiyama et al. |
| 5,330,906 | A | 7/1994 | Kajiyama et al. |
| 5,418,155 | A | 5/1995 | Cormier et al. |
| 5,439,797 | A | 8/1995 | Tsien et al. |
| 5,484,956 | A | 1/1996 | Lundquist et al. |
| 5,491,084 | A | 2/1996 | Chalfie et al. |
| 5,538,879 | A | 7/1996 | Muller-Rober et al. |
| 5,576,198 | A | 11/1996 | McBride et al. |
| 5,595,896 | A | 1/1997 | Coruzzi et al. |
| 5,618,722 | A | 4/1997 | Zenno et al. |
| 5,629,470 | A | 5/1997 | Lam et al. |
| 5,633,155 | A | 5/1997 | Kim et al. |
| 5,641,670 | A | 6/1997 | Treco et al. |
| 5,650,135 | A | 7/1997 | Contag et al. |
| 5,654,173 | A | 8/1997 | Jacobs et al. |
| 5,656,466 | A | 8/1997 | Moon et al. |
| 5,674,713 | A | 10/1997 | McElroy et al. |
| 5,674,731 | A | 10/1997 | Lin et al. |
| 5,688,648 | A | 11/1997 | Mathies et al. |
| 5,689,045 | A | 11/1997 | Logemann et al. |
| 5,689,049 | A | 11/1997 | Cigan et al. |
| 5,700,673 | A | 12/1997 | McElroy et al. |
| 5,707,804 | A | 1/1998 | Mathies et al. |
| 5,728,528 | A | 3/1998 | Mathies et al. |
| 5,733,761 | A | 3/1998 | Treco et al. |
| 5,739,409 | A | 4/1998 | Fischer et al. |
| 5,750,870 | A | 5/1998 | Mathews et al. |
| 5,767,367 | A | 6/1998 | Dudits et al. |
| 5,795,737 | A | 8/1998 | Seed et al. |
| 5,804,387 | A | 9/1998 | Cormack et al. |
| 5,824,485 | A | 10/1998 | Thompson et al. |
| 5,843,746 | A | 12/1998 | Tatsumi et al. |

(Continued)

FOREIGN PATENT DOCUMENTS

DE    19718640 A    7/1999
EP    0036776       9/1981

(Continued)

OTHER PUBLICATIONS

H. Guo et al., "Protein Tolerance to Random Amino Acid Change", PNAS 101(25): 9205-9210. (Jun. 2004).*
Shcherbo, D. et al., "Bright far-red fluorescent protein for whole-body imaging," Nat. Methods. (2007) 4:741-746.
Skolnick, J. et al., "From genes to protein structure and function: novel applications of computational approaches in the genomic era," TIBTECH (2000) 18:34-39.
Snapp, E.L. et al., "Formation of stacked ER cisternae by low affinity protein interactions," J. Cell. Bio. (2003) 163:257-269.
Sorensen, M. et al., "Rapidly maturing red fluorescent protein variants with strongly enhanced brightness in bacteria," FEBS Lett. (2003) 552(2-3):110-114.

(Continued)

*Primary Examiner* — Rebecca Prouty
(74) *Attorney, Agent, or Firm* — Valauskas Corder LLC

(57) ABSTRACT

Polynucleotides encoding variant polypeptides of DsRed are provided herein. The DsRed variants have increased bacterial expression, reduced aggregation, increased solubility, shifted emission spectra or increased brightness relative to a wild-type DsRed.

21 Claims, 17 Drawing Sheets

(56) References Cited

U.S. PATENT DOCUMENTS

| | | | |
|---|---|---|---|
| 5,863,727 | A | 1/1999 | Lee et al. |
| 5,866,336 | A | 2/1999 | Nazarenko et al. |
| 5,869,255 | A | 2/1999 | Mathies et al. |
| 5,874,304 | A | 2/1999 | Zolotukhin et al. |
| 5,911,952 | A | 6/1999 | Tsuji |
| 5,919,445 | A | 7/1999 | Chao |
| 5,945,283 | A | 8/1999 | Kwok et al. |
| 5,945,526 | A | 8/1999 | Lee et al. |
| 5,958,713 | A | 9/1999 | Thastrup et al. |
| 5,968,738 | A | 10/1999 | Anderson et al. |
| 5,968,750 | A | 10/1999 | Zolotukhin et al. |
| 5,976,796 | A | 11/1999 | Szalay et al. |
| 5,981,200 | A | 11/1999 | Tsien et al. |
| 5,985,577 | A | 11/1999 | Bulinski |
| 5,989,835 | A | 11/1999 | Dunlay et al. |
| 5,998,146 | A | 12/1999 | Latva et al. |
| 6,008,373 | A | 12/1999 | Waggoner et al. |
| 6,020,192 | A | 2/2000 | Muzyczka et al. |
| 6,066,476 | A | 5/2000 | Tsien et al. |
| 6,130,313 | A | 10/2000 | Li et al. |
| 6,306,600 | B1 | 10/2001 | Kain et al. |
| 7,005,511 | B2 | 2/2006 | Tsien et al. |
| 7,250,298 | B2 | 7/2007 | Glick et al. |
| 7,671,185 | B2 | 3/2010 | Glick et al. |
| 7,910,714 | B2 | 3/2011 | Glick et al. |
| 2002/0197676 | A1 | 12/2002 | Lukyanov et al. |
| 2003/0059835 | A1 | 3/2003 | Tsien et al. |
| 2003/0170911 | A1 | 9/2003 | Tsien et al. |
| 2005/0149994 | A1 | 7/2005 | Bevis et al. |
| 2006/0275827 | A1 | 12/2006 | Campbell et al. |

FOREIGN PATENT DOCUMENTS

| | | |
|---|---|---|
| EP | 0155476 | 9/1985 |
| EP | 0127839 | 7/1992 |
| EP | 0244234 | 7/1993 |
| WO | 87/00195 | 1/1987 |
| WO | 90/03430 | 4/1990 |
| WO | 90/04036 | 4/1990 |
| WO | 90/10077 | 9/1990 |
| WO | 91/00357 | 1/1991 |
| WO | 92/02190 | 2/1992 |
| WO | 99/15650 | 4/1999 |
| WO | 99/49019 | 9/1999 |
| WO | 00/02997 | 1/2000 |
| WO | 00/03246 | 1/2000 |
| WO | 00/17624 | 3/2000 |
| WO | 00/17643 | 3/2000 |
| WO | 00/26408 | 5/2000 |
| WO | 00/46233 | 8/2000 |
| WO | 01/27150 | 4/2001 |
| WO | 02/40539 | 5/2002 |
| WO | 02/068459 | 9/2002 |
| WO | 03/054158 | 7/2003 |
| WO | 2005/100387 | 10/2005 |
| WO | 2009/059305 | 5/2009 |

OTHER PUBLICATIONS

Terskikh, A. et al., "Fluorescent timer: protein that changes color with
Strack, R.L. et al., "A noncytotoxic DsRed variant for whole-cell labeling," Nature Methods (2008) 5(11):955-957.
Strongin, D.E. et al., "Structural rearrangements near to chromophore influence the maturation speed and brightness of DsRed variants," PEDS. (2007) 20:525-534.
Tao, W. et al., "Enhanced green fluorescent protein is a nearly ideal long-term expression tracer for hematopoietic stem cells, whereas DsRed-express fluorescent protein is not," Stem Cells (2007) 25(3):670-678. time," Science (2000) 290:1585-1588.
Terskikh, A.V. et al., "Analysis of DsRed mutants. Space around the fluorophore accelerates fluorescence development," J. Biol. Chem. (2002) 277(10):7633-7636.
Tsein, R.Y., "The green fluorescent protein," Annu. Rev. Biochem. (1998) 67:509-544.

Tsein, R.Y., "Rosy dawn for fluorescent proteins," Nat. Biotech. (1999) 17:956-957.
Tubbs, J.L. et al., "Crystallographic Structures of Discosoma Red Fluorescent Protein with Immature and Matur Chromophores: Linking Peptide Bond Trans-Cis Isomerization and Acylimine Formation in Chromophore Maturation," Biochem. (2005) 44:9833-9840.
Verkhusha, V.V. et al., "An enhanced mutant of red fluorescent protein DsRed for double labeling and developmental timer of neutral fiber bundle formation," J. Biol. Chem. (2001) 276(32)29621-29624.
Wall, M.A. et al., "The Structural Basis for Red Fluorescence in the Tetrameric GFP Homolog DsRed," Nat. Struct. Biol. (2000) 7:12:1133-1138.
Weiss, S., "Fluorescence Spectroscopy of Single Biomolecules," Science (1999) 283:1676-1683.
Wiehler, J. et al., "Mutants of Discosoma Red Fluorescent Protein with a GFP-like C+13158hromophore," FEBS Lett. (2001) 487:384-389.
Yang, T-T. et al., "Optimized codon usage and chromophore mutations provide enhanced sensitivity with the green fluorescent protein," Nucleic Acids Research (1996) 24(22):4592-4593.
Yanushevich et al., "A Strategy for the Generation of Non-aggregating Mutants of Anthozoa Fluorescent Proteins," FEBS Lett. (2002) 511:11-14.
Yarbrough, D. et al., "Refined crystal structure of DsRed, a red fluorescent protein from coral, at 2.0-A resolution," Proc. Natl. Acad. Sci. USA (2001) 98:2:462-467.
Zacharias, D.A. et al., "Partitioning of Lipid-Modified Monomeric GFPs into Membrane Microdomains of Live Cells," Science. (2002) 296:913-916.
Zeng, X. and Hu, J.C., "Detection of Tetramerization Domains in Vivo by Cooperative DNA Binding to Tandem 1 Operator Sites," Gene (1997) 185:245-249.
International Search Report, European Patent Office, PCT/US2008/082264 (Jul. 31, 2009).
Garcia-Parajo, M.F. et al., "Visualizing individual green fluorescent proteins with a near field optical microscope," Cytometry (1999) 36:239-246.
Heikal, A.A. et al., "Molecular spectroscopy and dynamics of intrinsically fluorescent proteins: coral red (dsRed) and yellow (Citrine)," Proc. Natl. Acad. Sci. (2000) 97(22):11986-12001.
Heim, R. et al., "Improved green fluorescence," Nature (1995) 373:663-664.
Moerner, W.E. et al., "Optical Methods for Exploring Dynamics of Single Copies of Green Fluorescent Protein," Cytometry (1999) 36:232-238.
Pedalacq, J. et al., "Engineering and characterization of a superfolder green fluorescent protein," Nat. Biotechnol. (2006) 24:79-88, 1170.
Pfleger, B.F. et al., "Optimization of DsRed production in *Escherichia coli*: effect of ribosome binding site sequestration on translation efficiency," Biotech. Bioeng. (2005) 92(5):553-558.
Phillips et al., "Structure and Dynamics of Green Fluorescent Protein," Curr. Opin. Struc. Biol. (1997) 7:821-827.
Pierce, D.W. and Vale, R.D., "Single-molecule fluorescence detection of green fluorescence protein and application to single-protein dynamics," Methods in Cell Biology (1999) Sullivan and Kay, eds., Academic Press, San Diego 5.
Piston, D.W., "Imaging Living Cells and Tissues by Two-Photon Excitation Microscopy," Trends Cell Biol. (1999) 9:66-69.
Radotic, K. et al., "Spontaneous ultraweak bioluminescence in plants: origins, mechanisms and properties," Gen. Physiol. Biophys. (1998) 17:289-308.
Remington, S.J., "Negotiating the Speed Bumps to Fluorescence," Nat. Biotechnol. (2002) 20:28-29.
Richarson, J.S. et al., "Natural β-sheet proteins use negative design to avoid edge-to-edge aggregation," PNAS. (2002) 99:2754-2759.
Schwille, P. et al., "Molecular dynamics in living cells observed by fluorescence correlation spectroscopy with one-and two-photon excitation," Biophys. J. (1999) 77:2251-2265.
Shaner, N.C. et al., "Improved monomeric red, orange and yellow fluorescent proteins derived from *Discosoma* sp. red fluorescent protein," Nat. Biotechnol. (2004) 22(12):1567-1572.
Shaner, N.C. et al., "A guide to choosing fluorescent proteins," Nat. Methods. (2005) 2:905-909.

(56) References Cited

OTHER PUBLICATIONS

Baird, G.S. et al., "Biochemistry, mutagenesis, and oligomerization of DsRed, a red fluorescent protein from coral," Proc. Natl. Acad. Sci. USA (2000) 97:11984-11989.

Beernink, P.T. et al., "Disruption of the aldolase A tetramer into catalytically active monomers," Proc. Natl. Acad. Sci. USA (1996) 93:5374-5379.

Bevis, B.J.et al., "Rapidly maturing variants of the *Discosoma* red fluorescent protein (DsRed)," Nat. Biotechnol. (2002) 20:83-87.

Bogan, A.A. and Thorn, K.S., "Anatomy of hot spots in protein interfaces," J. Mol. Biol. (1998) 280:1-9.

Campbell, R.E. et al., "A monomeric red fluorescent protein," Proc. Natl. Acad. Sci. USA (2002) 99(12):7877-7882.

Condeelis, J.S. et al., "Imaging of Cancer Invasion and Metastasis Using Green Fluorescent Protein," Eur. J. Cancer (2000) 36:1671-1680.

Cormack, B.P. et al., "FACS-optimized Mutants of the Green Fluorescent Protein (GFP)," Gene (1996) 173:33-38.

Cronin et al., "A Genetics-Friendly GFP Assay," Trends Cell Biol. (1999) 9:36.

Cubitt, A.B. et al., "Understanding Structure-Function Relationships in the Aequoria victoria Green Fluorescent Protein," Methods in Cell Biology (1999) 58:19-30.

De Giorgi, F. et al., "Targeting GFP to organelles," Methods in Cell Biology (1999), Sullivan and Kay, eds., Academic Press, San Diego, 58:75-85.

Deo et al., "Luminescent Proteins from *Aequorea victoria*: Applications in Drug Discovery and in High Throughput Analysis," Fresenius J. Anal. Chem. (2001) 369:258-266.

Dickson, R.M. et al., "On/off Blinking and Switching Behavior of Single Molecules of Green Fluorescent Protein," Nature (1997) 388:355-358.

Dittrich, P. et al., "Accessing molecular dynamics in cells by fluorescence correlation spectroscopy," Biol. Chem. (2001) 382:491-494.

Dove, S.G. et al., "Isolation and partial characterization of the pink and blue pigments of pocilloporid and acroporid corals," Biol. Bull. (1995) 189:288-297.

Ellenberg, J. et al., "Dual-color imaging with GFP variants," Trends Cell Biol.(1999) 9:52-56.

Fischer et al., "A Brilliant Monomeric Red Fluorescent Protein to Visualize Cytoskeleton Dynamics in Dictyostelium," FEBS Letters (2004) 577:277-232.

Fradkov, A.F. et al., "Novel fluorescent protein from *Discosoma* coral and its mutants possesses a unique far-red fluorescence," FEBS Lett. (2000) 479:127-130.

Garcia-Parajo, M.F. et al., "The Nature of Fluorescence Emission in the Red Fluorescent Protein DsRed, Revealed by Single-molecule Detection," Proc. Natl. Acad. Sci. USA (2001) 98:14392-14397.

Gross, L.A. et al., "The structure of the chromophore within DsRed, a red fluorescent protein from coral," Proc. Natl. Acad. Sci. USA (2000) 97:22:11990-11995.

Gurskaya, N.G. et al., "Color transitions in coral's fluorescent proteins by site-directed mutagenesis," BMC Biochem. (2001) 2:6.

Harms, G.S. et al., "Autofluorescent proteins in single-molecule research: applications to live cell imaging microscopy," Biophys. J. (2001) 80:2396-2408.

Haugwitz, M. et al., "Characterization of the improved red fluorescent protein DsRed2," Soc. for Neuroscience Abstracts(2001) 27(1):351.

Hawley, T.S. et al., "Four-color flow cytometric detection of retrovirally expressed red, yellow, green, and cyan fluorescent proteins," BioTechniques (2001) 30:1028-1034.

Heim, R. and Tsien, R.Y., "Engineering green fluorescent protein for improved brightness, longer wavelengths and fluorescent resonance energy transfer," Curr. Biol. (1996) 6:2:178-182.

Klasen, M. et al., "Silent point mutation in DsRed resulting in enhanced relative fluorescence intensity," Biotechniques (2004) 36(2):236-238.

Knop et al., "Improved Version of the Red Fluorescent Protein (drFP583/DSRed/RFP)," BioTechniques (2002) 33:3:592,594,596-598,600,602.

Kubitscheck, U. et al., "Imaging and Tracking of Single GFP Molecules in Solution," Biophys. J. (2000) 78:2170-2179.

Lauf, U. et al., "Expression of Fluorescently Tagged Connexins: a Novel Approach to Rescue Function of Oligomeric DsRed-tagged Proteins," FEBS Lett. (2001) 498-11-15.

Lukyanov, K. et al., "Natural animal coloration can be determined by a nonfluorescent green fluorescent protein homolog," J. Biol. Chem. (2000) 275(34):25879-25882.

Macek, P. et al., "Intrinsic tryptophan fluorescence of equinatoxin II, a pore-forming polypeptide from the sea anemone *Actinia equina* L, monitors its interaction with lipid membranes," Eur. J. Biochem. (1995) 234:329-335.

Martynov, V.I. et al., "Alternative cyclization in GFP-like proteins family," J. Biol. Chem. (2001) 276:24: B12521012-21016.

Matz, M.V. et al., "Fluorescent proteins from nonbioluminescent Anthozoa species," Nat. Biotechnol. (1999) 17:969-973.

Miyawaki, A. et al., "Fluorescent Indicators for Ca2+ Based on Green Fluorescent Proteins and Calmodulin," Nature (1997) 388:882-887.

Mizuno, H. et al., "Red fluorescent protein from *Discosoma* as a fusion tag and a partner for fluorescence resonance energy transfer," Biochem. (2001) 40:2502-2510.

\* cited by examiner

| | 1 | | | | | 50 | |
|---|---|---|---|---|---|---|---|
| Plum | MVSKGEE... | .VIKEFMRFK | EHMEGSVNGH | EFEIEGEGEG | RPYEGTQTAR | | (SEQ ID NO:17) |
| rasberry | MVSKGEE... | .VIKEFMRFK | VRMEGSVNGH | EFEIEGEGEG | RPYEGTQTAK | | (SEQ ID NO:18) |
| mHoneyDew | .MASSED... | .VIKEFMRFK | VRMEGSVNGH | EFEIEGEGEG | RPYEGTQTAK | | (SEQ ID NO:19) |
| mtangerine | .MASSED... | .VIKEFMRFK | VRMEGSVNGH | EFEIEGEGEG | RPYEGTQTAK | | (SEQ ID NO:20) |
| dTomato | MVSKGEE... | .VIKEFMRFK | VRMEGSMNGH | EFEIEGEGEG | RPYEGTQTAK | | (SEQ ID NO:21) |
| mBanana | MVSKGEENNM | AVIKEFMRFK | VRMEGSVNGH | EFEIEGEGEG | RPYEGTQTAK | | (SEQ ID NO:22) |
| strawberry | MVSKGEENNM | AIIKEFMRFK | VRMEGSVNGH | EFEIEGEGEG | RPYEGTQTAK | | (SEQ ID NO:23) |
| mOrange | MVSKGEENNM | AIIKEFMRFK | VRMEGSVNGH | EFEIEGEGEG | RPYEGFQTAK | | (SEQ ID NO:24) |
| mCherry | MVSKGEEDNM | ALIKEFMRFK | VHMEGSVNGH | EFEIEGEGEG | RPYEGTQTAK | | (SEQ ID NO:25) |
| mRFP1 | .MASSED... | .VIKEFMRFK | VRMEGSVNGH | EFEIEGEGES | RPYEGTQTAK | | (SEQ ID NO:26) |
| mRFP1-1 | ..DNTED... | .VIKEFMQFK | VRMEGSVNGH | YFEIEGEGEG | RPYEGTQTAK | | (SEQ ID NO:27) |
| DsRed_Monomer | .MASSED... | .VIKEFMRFK | VRMEGSVNGH | EFEIEGEGEG | KPYEGTQTAK | | (SEQ ID NO:28) |
| DsRedExpress | .MASSED... | .VITEFMRFK | VRMEGTVNGH | EFEIEGEGEG | RPYEGHNTVK | | (SEQ ID NO:29) |
| DsRed2 | .MASSEN... | .VITEFMRFK | VRMEGSVNGH | EFEIEGEGEG | RPYEGHNTVK | | (SEQ ID NO:30) |
| DsRed1-wt | .MRSSKN... | .VIKEFMRFK | VRMEGTVNGH | EFEIEGEGEG | RPYEGHNTVK | | (SEQ ID NO:31) |

| | 51 | | | | | 100 | |
|---|---|---|---|---|---|---|---|
| Plum | LKVTKGGPLP | FAWDILSPQI | MYGSKAYVKH | PADIPDYLKL | SFPEGFKWER | | |
| rasberry | LKVTKGGPLP | FAWDILSPQC | MYGSKGYVKH | PADIPDYLKL | SFPEGFKWER | | |
| mHoneyDew | LKVTKGGPLP | FAWDILSPQF | MWGSKAYVKH | PADIPDYLKL | SFPEGFKWER | | |
| mtangerine | LKVTKGGPLP | FAWDILSPQF | CYGSKAYVKH | PADIPDYKKL | SFPEGFKWER | | |
| dTomato | LKVTKGGPLP | FAWDILSPQF | MYGSKAYVKH | PADIPDYLKL | SFPEGFKWER | | |
| mBanana | LKVTKGGPLP | FAWDILTPNF | CYGSKAYVKH | PTGIPDYFKL | SFPEGFKWER | | |
| strawberry | LKVTKGGPLP | FAWDILTPNF | TYGSKAYVKH | PADIPDYLKL | SFPEGFKWER | | |
| mOrange | LKVTKGGPLP | FAWDILSPQF | TYGSKAYVKH | PADIPDYFKL | SFPEGFKWER | | |
| mCherry | LKVTKGGPLP | FAWDILSPQF | MYGSKAYVKH | PADIPDYLKL | SFPEGFKWER | | |
| mRFP1 | LKVTKGGPLP | FAWDILSPQF | QYGSKAYVKH | PADIPDYLKL | SFPEGFKWER | | |
| mRFP1-1 | LQVTKGGPLP | FAWDILSPQF | MYGSKAYVKH | PADIPDYLKL | SFPEGFTWER | | |
| DsRed_Monomer | LKVTKGGPLP | FAWDILSPQF | QYGSKVYVKH | PADIPDYMKL | SFPEGFKWER | | |
| DsRedExpress | LKVTKGGPLP | FAWDILSPQF | QYGSKVYVKH | PADIPDYKKL | SFPEGFKWER | | |
| DsRed2 | LKVTKGGPLP | FAWDILSPQF | QYGSKVYVKH | PADIPDYKKL | SFPEGFKWER | | |
| DsRed1-wt | LKVTKGGPLP | FAWDILSPQF | QYGSKVYVKH | PADIPDYKKL | SFPEGFKWER | | |

| | 101 | | | | | 150 | |
|---|---|---|---|---|---|---|---|
| Plum | VMNFEDGGVV | TVTQDSSLQD | GEFIYKVKVR | GTNFPSDGPV | MQKKTMGWEA | | |
| rasberry | VMNFEDGGVV | TVTQDSSLQD | GEFIYKVKLR | GTNFPPSDGPV | MQKKTMGWEA | | |
| mHoneyDew | VMNFEDGGVV | TVTQDSSLQD | GEFIYKVKLR | GTNFPSDGPV | MQKKTMGWAA | | |
| mtangerine | VMNFEDGGVV | TVTQDSSLQD | GEFIYKVKLR | GTNFPSDGPV | MQKKTMGWEA | | |
| dTomato | VMNFEDGGIV | TVAQDSSLQD | GTLIYKVKMR | GTNFPPDGPV | MQKKTMGWEA | | |
| mBanana | VMNFEDGGVV | TVTQDSSLQD | GEFIYKVKLR | GTNFPSDGPV | MQKKTMGWEA | | |
| strawberry | VMNFEDGGVV | TVTQDSSLQD | GEFIYKVKLR | GTNFPPSDGPV | MQKKTMGWEA | | |
| mOrange | VMNFEDGGVV | TVTQDSSLQD | GEFIYKVKLR | GTNFPPSDGPV | MQKKTMGWEA | | |
| mCherry | VMNFEDGGVV | TVTQDSSLQD | GEFIYKVKLR | GTNFPPSDGPV | MQKKTMGWEA | | |
| mRFP1 | VMNFEDGGVV | TVTQDSSLQD | GEFIYKVKLR | GTNFPSDGPV | MQKKTMGWEA | | |
| mRFP1-1 | VMNFEDGGVV | TVTQDSSLQD | GEFIYKVKLR | GTNFPSDGPV | MQKKTMGWEA | | |
| DsRed_Monomer | SMNFEDGGVV | EVQQDSSLQD | GTFIYKVKFK | GVNFPADGPV | MQKKTMGWEP | | |
| DsRedExpress | VMNFEDGGVV | TVTQDSSLQD | GSFIYKVKFI | GVNFPSDGPV | MQKKTMGWEA | | |
| DsRed2 | VMNFEDGGVA | TVTQDSSLQD | GCFIYKVKFI | GVNFPSDGPV | MQKKTMGWEA | | |
| DsRed1-wt | VMNFEDGGVV | TVTQDSSLQD | GCFIYKVKFI | GVNFPSDGPV | MQKKTMGWEA | | |

FIG. 16A

|  | 151 |  |  |  | 200 |  |
|---|---|---|---|---|---|---|
| Plum | SSERMYPEDG | ALKGEMKNRL | RLKDGGHYDA | EVKTTYMAKK | PVQLPGAYKT | (SEQ ID NO:17) |
| rasberry | SSERMYPEDG | ALKGEMKMRL | KLKDGGHYDA | EVKTTYMAKK | PVQLPGAYKT | (SEQ ID NO:18) |
| mHoneyDew | TTERMYPEDG | ALKGEIKMRL | KLKDGGHYDA | EVKTTYMAKK | PVQLPGAYKI | (SEQ ID NO:19) |
| mtangerine | SSERMYPEDG | ALKGEIKMRL | KLKDGGHYDA | EVKTTYMAKK | PVQLPGAYKT | (SEQ ID NO:20) |
| dTomato | STERLYPRDG | VLKGEIHQAL | KLKDGGHYLV | EFKTTYMAKK | PVQLPGYYYV | (SEQ ID NO:21) |
| mBanana | SSERMYPEDG | ALKGEIKMRL | KLKDGGHYSA | ETKTTYKAKK | PVQLPGAYIA | (SEQ ID NO:22) |
| strawberry | SSERMYPEDG | ALKGEIKMRL | KLKDGGHYDA | EVKTTYKAKK | PVQLPGAYIV | (SEQ ID NO:23) |
| mOrange | SSERMYPEDG | ALKGEIKMRL | KLKDGGHYTS | EVKTTYKAKK | PVQLPGAYIV | (SEQ ID NO:24) |
| mCherry | SSERMYPEDG | ALKGEIKQRL | KLKDGGHYDA | EVKTTYKAKK | PVQLPGAYNV | (SEQ ID NO:25) |
| mRFP1 | STERMYPEDG | ALKGEIKMRL | KLKDGGHYDA | EVKTTYMAKK | PVQLPGAYKT | (SEQ ID NO:26) |
| mRFP1-1 | SSERMYPEDG | ALKGEIKMRL | KLKDGGHYDA | EVKTTYMAKK | PVQLPGAYKT | (SEQ ID NO:27) |
| DsRed_Monomer | STEKLYPQDG | VLKGEISHAL | KLKDGGHYTC | DFKTVYKAKK | PVQLPGNHYV | (SEQ ID NO:28) |
| DsRedExpress | STERLYPRDG | VLKGEIHKAL | KLKDGGHYLV | EFKSIYMAKK | PVQLPGYYYV | (SEQ ID NO:29) |
| DsRed2 | STERLYPRDG | VLKGETHKAL | KLKDGGHYLV | EFKSIYMAKK | PVQLPGYYYV | (SEQ ID NO:30) |
| DsRed1-wt | STERLYPRDG | VLKGEIHKAL | KLKDGGHYLV | EFKSIYMAKK | PVQLPGYYYV | (SEQ ID NO:11) |

|  | 201 |  |  | 239 |
|---|---|---|---|---|
| Plum | DIKLDITSHN | EDYTIVEQYE | RAEGRHSTGA | ......... |
| rasberry | DIKLDITSHN | EDYTIVEQYE | RAEGRHSTGA | ......... |
| mHoneyDew | DGKLDITSHN | EDYTIVEQYE | RAEGRHSTGA | ......... |
| mtangerine | DIKLDITSHN | EDYTIVELYE | RAEGRHSTGA | ......... |
| dTomato | DTKLDITSHN | EDYTIVEQYE | RSEGRHHLFL | YGMDELYK. |
| mBanana | GEKIDITSHN | EDYTIVELYE | RAEGRHSTGG | M..DELYK. |
| strawberry | GIKLDITSHN | EDYTIVELYE | RAEGRHSTGG | M..DELYK. |
| mOrange | GIKLDITSHN | EDYTIVEQYE | RAEGRHSTGG | M..DELYK. |
| mCherry | NIKLDITSHN | EDYTIVEQYE | RAEGRHSTGA | ......... |
| mRFP1 | DIKLDITSHN | EDYTIVEQYE | RAEGRHSTGA | ......... |
| mRFP1-1 | DSKLDITNHN | EDYTIVEQYE | HAEARHSGSQ | ......... |
| DsRed_Monomer | DSKLDITSHN | EDYTIVEQYE | RAEGRHHLFL | ......... |
| DsRedExpress | DAKLDITSHN | EDYTIVEQYE | RTEGRHHLFL | ......... |
| DsRed2 | DSKLDITSHN | EDYTIVEQYE | RTEGRHHLFL | ......... |
| DsRed1-wt | DSKLDITSHN | EDYTIVEQYE | RTEGRHHLFL | ......... |

FIG. 16B

RED FLUORESCENT PROTEINS WITH ENHANCED BACTERIAL EXPRESSION, INCREASED BRIGHTNESS AND REDUCED AGGREGATION

CROSS-REFERENCE TO RELATED APPLICATIONS

This application is a national stage filing under 35 U.S.C. 371 of International Application No. PCT/US2008/082264, filed Nov. 3, 2008, which claims priority to U.S. Provisional Patent Application Ser. No. 60/984,642, filed on Nov. 1, 2007. Each of these applications is incorporated herein by reference in its entirety.

STATEMENT REGARDING FEDERALLY SPONSORED RESEARCH

This invention was made with government support under National Institutes of Health grant numbers R01 GM65389 to Glick and R01 EB008087 to Glick and Keenan. The government has certain rights in the invention.

INTRODUCTION

Fluorescent proteins, such as green fluorescent protein (GFP), are invaluable tools used in pure and applied research. Although fluorescent proteins have been widely available for a relatively short time, they have had an important impact on biomedical research, contributing to our understanding of basic cellular and developmental processes that underlie health and disease. GFP and its relatives are widely used for medically-oriented research. For example, GFP has been used to analyze bacterial gene expression during infection, to visualize tumor cell behavior during metastasis, and to monitor GFP fusion proteins in gene therapy studies. Fluorescent proteins are also useful in high-throughput screens for drug discovery.

A red fluorescent protein produced by the coral *Discosoma* and designated DsRed (wild-type DsRed) is potentially useful, e.g., as a fluorescent reporter protein or as a fusion tag. DsRed features many properties that make it an ideal fluorescent marker. First, DsRed fluorescence is bright and can be excited and detected using commonly available filter sets or lasers. Second, DsRed is excited by lower energy light compared to GFP and its derivatives, so cells accrue less photodamage and experience less phototoxicity under DsRed imaging conditions. Third, light scattering makes it difficult to image thick tissue samples with conventional fluorescence microscopy, but the wavelengths of light for DsRed excitation and emission are scattered less than those for GFP. Finally, the DsRed excitation and emission spectra are well separated from those of GFP, permitting simple two-color imaging or FRET. However, wild-type DsRed suffers from certain drawbacks.

First, the maturation process that yields the red fluorophore is slow, with a half-time of ~12 h at 37° C. Second, wild-type DsRed occurs as a homotetramer, which makes its use as a fluorescent reporter in a fusion protein problematic. For example, tetramerization of the DsRed fusion protein may interfere with or perturb the function or localization of the protein. In addition, DsRed tetramers undergo higher-order aggregation. Fusion of DsRed to membrane proteins or to oligomeric proteins often produces large aggregates. Monomeric DsRed variants have been made, but are not as bright or as photostable as the DsRed tetramers. The available DsRed tetramer variants still form higher order aggregates and can cause cellular toxicity.

There is, therefore, ongoing interest in developing new fluorescent protein labels with improved characteristics as experimental and clinical tools.

SUMMARY

Isolated polynucleotides encoding variant polypeptides of DsRed are provided. The polynucleotides include an AGC codon encoding a serine at amino acid position 3 of the variant polypeptide and the variant polypeptide includes at least one amino acid substitution selected from the group consisting of A2D and S4T. The polynucleotides demonstrate increased bacterial expression relative to a wild-type DsRed.

In another aspect, isolated polynucleotides encoding variant polypeptides of DsRed having reduced aggregation relative to wild-type DsRed are provided. The variant polypeptides include at least one amino acid substitution selected from the group consisting of E10P and Q188K.

In yet another aspect, isolated polynucleotides encoding variant polypeptides of a monomeric DsRed having increased brightness relative to DsRed.M1 are provided. The variant polypeptides include amino acid substitution K121H.

In still another aspect, isolated polynucleotides encoding variant polypeptides of DsRed, having increased brightness and reduced aggregation relative to wild-type DsRed or DsRed.M1 are described. The variant polypeptides include amino acid substitutions W58Y and I29V.

In a further aspect, isolated polynucleotides encoding variant polypeptides of a DsRed having increased brightness and reduced aggregation relative to wild-type DsRed or DsRed.M1 are described. The variant polypeptides include amino acid substitutions D115G and G116D.

In a still further aspect, isolated polynucleotides encoding variant polypeptides of DsRed having a blue-shifted emission spectra relative to wild-type DsRed are disclosed. The variant polypeptides include a substitution at amino acid 213. Alternatively, the variant polypeptides include a threonine substitution at amino acid 66.

In yet another aspect, isolated polynucleotides encoding variant polypeptides of DsRed having increased solubility relative to the starting DsRed polypeptide are provided. The variant polypeptide comprises at least one amino acid substitution selected from L85Q, D128N, D128K, E160D, S162N, and K198E.

In still another aspect, isolated polynucleotides encoding variant polypeptides of DsRed having increased brightness relative to a comparable polypeptide lacking the amino acid substitution are disclosed. The variant polypeptide includes an amino acid substitution selected from the group consisting of V73T, V73A, H75C, H75K, H75R, K83F, M83F, and V175C. Alternatively, the variant polypeptides may include amino acid substitutions F177V and Q66M. Alternatively, the variant polypeptide may include amino acid substitutions L150M, F177V, and S197I.

In a further aspect, isolated polynucleotides encoding variant polypeptides of DsRed comprising an amino acid substitution of A44V are provided. The variant polypeptides have an emission spectra that is red-shifted as compared to the comparable polypeptide lacking the amino acid substitution.

BRIEF DESCRIPTION OF THE DRAWINGS

FIG. 8a is a bar graph showing HeLa cells transduced with lentiviruses encoding the indicated fluorescent proteins or a control lentivirus lacking a fluorescent protein gene. At days 3 and 10 post transduction, three wells of each transduction was harvested and detected using a 488-nm laser and a FITC filter set or a 543-nm laser and a PE filter set. The average fluorescent signals relative to control are plotted.

FIG. 8b is a bar graph showing the percentage of viable cells that were fluorescent from FIG. 8a.

FIG. 8c is a graph showing the that cells transduced with a lentiviral vector comprising a fluorescent protein are capable of replicating in culture.

FIG. 16 (SEQ ID NOS: 17 through 31) is a sequence alignment showing the amino acid sequences of several DsRed derived proteins. Conserved residues share a light gray shading.

DETAILED DESCRIPTION

Figure 1:
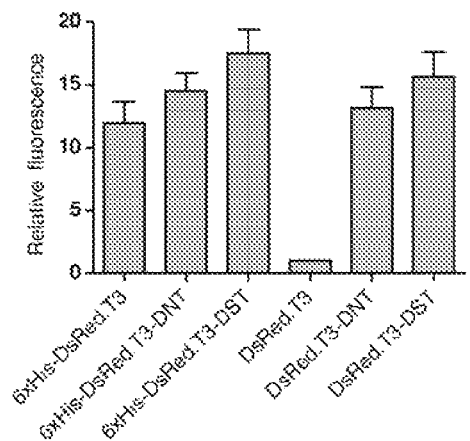
FIG. 1a is a bar graph comparing relative fluorescence of various DsRed variants.
FIG. 1b is a photograph of a Coomassie stained gel comparing the protein expression of various DsRed variants.
Figure 1:
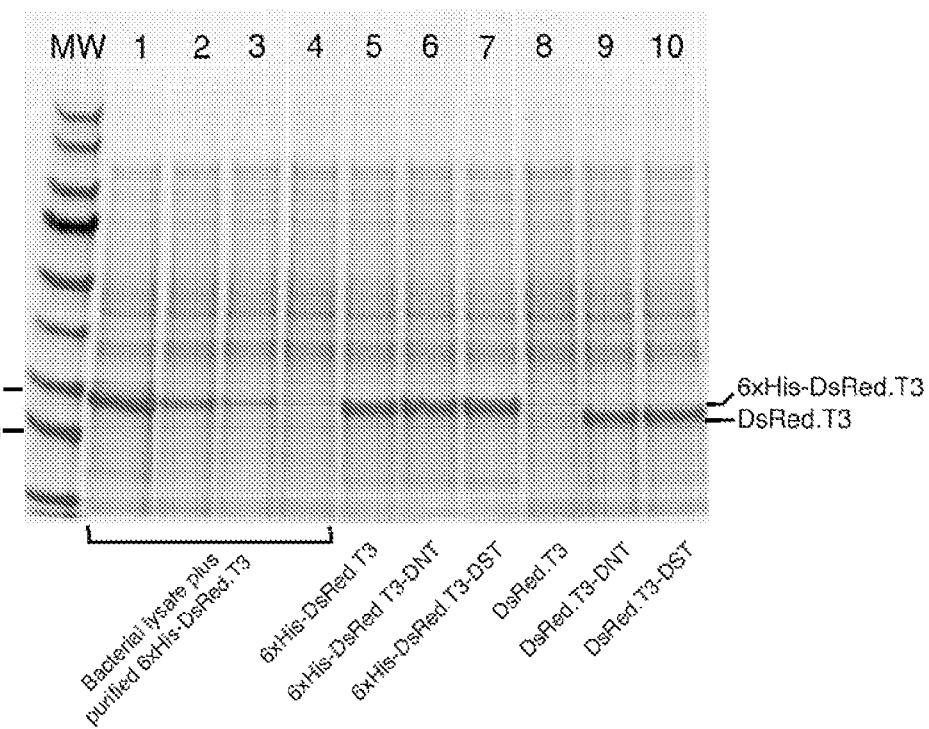

Polypeptide variants of wild-type *Discosoma* sp. red fluorescent protein (DsRed) are provided. Wild-type DsRed forms oligomers (e.g., dimers or tetramers) under physiologic conditions, which, in the native polypeptide, appears to play a role in its fluorescence activity. In addition, the tetramers aggregate to form higher order structures. A coding sequence for wild-type *Discosoma* sp. red fluorescent protein (DsRed) is shown in SEQ ID NO:11, and the amino acid sequence of wild-type DsRed is shown in SEQ ID NO:1. Monomeric DsRed polypeptides have been developed but suffer from reduced brightness and aggregation. The polypeptide variants provided herein have a reduced tendency to aggregate relative to wild-type DsRed and the previously characterized DsRed variants. Both monomeric and tetrameric variant DsRed polypeptides with reduced aggregation are provided. Reduced aggregation results in increased solubility. This reduced tendency to aggregate may be assessed by any suitable means, whether in vivo or in vitro. Several methods are described in the Examples below.

Other polypeptide variants provided herein have increased expression and/or increased brightness and or shifted excitation, emission, or absorbance spectra as compared to the tetrameric or monomeric variants from which they were derived. Increased bacterial expression was assessed as described in the Examples below. Any suitable means may be used to measure expression levels of the polypeptides in bacteria, or in other cell types, such as HeLa cells or Bone marrow derived cells. Those of skill in the art will appreciate many different methods may be used. Brightness of the fluorescent proteins may also be measured in a variety of ways, including but not limited to the methods described in the Examples. Increased brightness includes, but is not limited to increased relative brightness as measured by FACS analysis, increased maturation rate, increased molar extinction coefficient, increased quantum yield, increased photostability, etc. Increased bacterial expression, increased brightness, and spectral shift may also be assessed by any suitable means, whether in vivo or in vitro. Those of skill in the art will appreciate that many methods, including those described in the Examples, may be used to measure the expression, brightness and spectrum of the proteins.

Specific amino acid substitutions or combinations of substitutions are disclosed as reducing aggregation, increasing expression, increasing brightness, and/or altering the excitation emission or absorbance spectrum of DsRed variants. Those of skill in the art will appreciate that the various amino acid substitutions disclosed herein may be combined with each other or used with other amino acid substitutions to produce DsRed variants with reduced aggregation, increased brightness, increased expression in bacteria or other cells, and shifted excitation, emission, and/or absorbance spectra. For example FIG. 16 shows amino acid sequence alignments for several variant DsRed polypeptides. These polypeptides contain a variety of mutations. Those of skill in the art may use the information provided herein to generate DsRed variants comprising amino acid substitutions described herein in combination with amino acid substitutions known previously to generate DsRed variants with improved properties, i.e. improved expression, brightness, reduced aggregation. Amino acid substitutions demonstrated to reduce aggregation, increase brightness or increase expression in the tetrameric DsRed are expected to have similar effects in monomeric DsRed variants and vice versa, unless otherwise indicated. Such variants are also encompassed by the present invention.

Polypeptide variants were genetically engineered, as described in detail below, by altering a sequence encoding a rapidly maturing tetrameric variant of wild-type DsRed, designated DsRed.T3 (SEQ ID NO:3) or a monomeric variant of wild-type DsRed designated DsRed.M1 (SEQ ID NO:6). DsRed.T3 is described in further detail in co-pending U.S. patent application Ser. No. 10/844,064, which is incorporated herein by reference in its entirety. DsRed.M1 is described in further detail in U.S. Pat. No. 7,250,298, which is incorporated herein by reference in its entirety. The amino acid substitutions described herein may be used with other DsRed variants, such as DsRed.T1, DsRed.T4, mCherry, DsRed.M1, etc. (See FIG. 16).

The polypeptide variants described herein exhibit detectable fluorescence, suitably the fluorescence is within the red portion of the spectrum. By "detectable fluorescence" it is meant that the fluorescence at least partially overlaps the emission spectra of wild-type DsRed and is distinguishable over background. As indicated below, several of the variant DsRed polypeptides disclosed have maximal excitation and emission spectra that are shifted relative to the excitation and emission spectra of wild-type DsRed. Fluorescence may be detected by any suitable means including those known to persons of skill in the art, including, but not limited to, microscopy, spectroscopy, fluorescence activated cell sorting analysis (FACS).

Variant DsRed polypeptides having increased expression relative to wild-type DsRed are disclosed. Increased expression is suitably observed in any cell type including, but not limited to bacterial cells, plant cells and animal cells. Suitable animal cells include mammalian cells such as mouse cells or human cells. Suitably increased bacterial expression relative to wild-type DsRed is observed. Increased bacterial expression may be measured by any suitable method, such as those methods known to persons of skill in the art and includes, but is not limited to, the methods used in Example 2 below. Increased bacterial expression indicates that bacterial expression of the variant is increased by at least 10%, at least 20%, at least 30%, at least 40%, at least 50%, at least 60%, at least 70% or more above expression of the sequence from which the variant was derived or the wild-type DsRed. Bacterial expression may be increased by 2 fold, 5 fold, 10 fold, 15 fold, 20 fold or more in variants as compared to the sequence from which the variant was derived or wild-type DsRed. Several mutations resulted in increased bacterial expression. The first was a silent mutation at position 3 in the context of at least one of two other amino acid substitutions at position 2 and 4. The amino acid substitutions incorporated were A2D, S3S$^{AGC}$, and S4T. Alternatively, DsRed variants with amino acid substitutions A2D, S3N, and S4T also had increased bacterial expression. Two other silent mutations were also found to increase bacterial expression. The first is at amino acid position 164 in which the alanine is encoded by the nucleotide codon GCG in the variant polynucleotide to increase expression. In addition, when amino acid position 179 is encoded by the nucleotide codon TCA in the polynucleotide, mammalian expression of the variant polypeptide is increased.

Variant DsRed polypeptides having reduced aggregation are also disclosed. Reduced aggregation indicates that the variant DsRed has reduced interaction between the exposed surfaces of one polypeptide with another. Reduced aggregation in variant DsRed polypeptides that form tetramers means that the tetramers are less likely to form higher order aggregates. Reduced aggregation in variant monomer DsRed polypeptides means that the monomers are less likely to form dimers, tetramers or other higher order aggregates. The tendency of DsRed variants to aggregate may be measured by any suitable assay including those known to persons of skill in art. In the Examples, methods of assessing aggregation in tetramers and monomers are disclosed. The variants with reduced aggregation show less than about 90%, less than about 80%, less than about 70%, less than about 60%, less than about 50%, less than about 40%, less than about 30%, less than about 25%, less than about 20%, less than about 15%, less than about 10%, or less than about 5% of the aggregation shown by its corresponding aggregating analogue under the same conditions.

The following amino acid substitutions were identified as reducing aggregation in the tetramer either singly or in combinations: D6N, E10P, R17H, R36K, K47Q, K121H, M141L, D169G, Q188K, I210V, or L225Q. These amino acid substitutions also reduce aggregation of monomers of DsRed. Several of these amino acid substitutions are already present in DsRed.M1. In particular, the amino acid substitutions E10P and Q188K are each independently capable of reducing aggregation as compared to the corresponding polypeptide lacking the substitution. The following amino acid substitutions were identified as reducing aggregation in the monomer: L85Q, S96T, N98T, D115G, G116D, D128N, D128K, E160D, S162N, D176N, and K198E. In particular, the combination of D115G and G116D reduces aggregation. The amino acid substitutions E160D and S162N were also shown in the Examples to reduce aggregation. In addition, the amino acid substitutions W58Y and I29V in combination may also reduce aggregation.

Variant DsRed polypeptides having increased brightness are also disclosed. Increased brightness is a generic term and includes optimization of the excitation spectra, increasing the molar extinction coefficient and/or increasing the quantum yield. Brightness may be measured by any suitable means including those known to persons of skill in the art. Brightness was measured using several assays in the Examples. Brightness may be increased by 2 fold, 5 fold, 10 fold, 15 fold, 20 fold, 25 fold or more in the variants as compared to the corresponding analogue under the same conditions.

The following amino acid substitutions were identified as increasing brightness in the tetramer: Q66M, V73T, V175C and G219A. The following amino acid substitutions were identified as increasing brightness in the monomer: D6N, R17Y, A44V, Q66M, V73A, V73S, V73T, H75R, M83L, M83F, D115G, G116D, K121H, F124V, M141L, L150M, H163M, K168E, D169G, T174N, F177V, S197I, N203S, Q213L, A217S, Notably, several of these substitutions were identified above as reducing aggregation as well. These amino acid substitutions identified as increasing brightness in the monomer are likely to have a similar effect in tetramers and vice versa due to the conserved nature of the chromophore in the monomer and tetramer.

Several other amino acid substitutions that improve the functionality of the variant DsRed polypeptides are also disclosed. T217A and T217S provide stability. K83 can be substituted with any large hydrophobic amino acid and is needed to stabilize the monomer. Q213L and M66T are blue-shifting substitutions and could be used to produce an orange fluorescent protein that is photostable.

The amino acid substitutions indicated above are all exemplified in the Examples below. Those of skill in the art will appreciate that other amino acids similar to the substituted amino acids could be used at the amino acid positions indicated above and that those substitutions would be expected to have a similar effect on the resulting DsRed protein. For example, if a hydrophobic amino acid was substituted with a hydrophilic amino acid and demonstrated to reduce aggregation of the resulting protein, then one of skill in the art would expect that substitution with a different hydrophilic amino acid would also result in reduced aggregation.

The variant polypeptides provided herein are variants of wild-type DsRed and the previously characterized DsRed mutant proteins including, but not limited to, DsRed.T1, DsRed.T3 and DsRed.M1. Suitably, the variant polypeptides have the characteristics conferred by the mutation (e.g., increased bacterial expression, increased brightness or reduced aggregation) and have at least 60% amino acid identity to the wild-type or previously characterized DsRed proteins. Suitably the percent amino acid identity is at least 65%, at least 70%, at least 75%, at least 80%, at least 85%, at least 90%, or at least 95%. The polynucleotides encoding the polypeptides described herein may have a much lower percent identity due to the degeneracy of the genetic code. As shown in FIG. 16, DsRed proteins comprising a wide variety of amino acid substitutions have been identified and thus those skilled in the art will understand that Dsred proteins tolerate a significant number of substitutions.

Methods of using fluorescent proteins and the polynucleotides encoding these proteins are well known to persons of skill in the art. Several methods are described in the Examples. For example, the DsRed variants may be used to monitor expression of the variant polypeptide from a promoter of interest or as part of a fusion protein. The variant polypeptides may be used to monitor the location of the variant within a cell or within an animal. The variant polypeptide may be used to monitor the timing of expression within a cell or animal. Many additional uses are known to persons skilled in the art.

Also provided are fusion proteins encoded by the disclosed polynucleotides, which encode variant DsRed polypeptides linked to polynucleotides encoding polypeptides of interest. The polynucleotides are linked in such a way that the resulting proteins are co-expressed as a fusion protein and the polypeptide of interest is tagged with the fluorescent variant DsRed polypeptide. For example, the polynucleotides may be directly linked by a phosphodiester bond or they may be linked via a spacer region which keeps the polynucleotides in frame with each other such that the polypeptides are translated correctly. Fusion proteins may be used for any purpose, including but not limited to those uses currently known to those of skill in the art.

The polynucleotides disclosed herein may be used to make constructs in which the polynucleotides are operably connected to a promoter functional in a cell, such that when the construct is introduced into a cell, the polynucleotide is expressed and the variant polypeptides are produced. Also disclosed are cells comprising these polynucleotides and constructs, as well as vectors comprising the constructs. The cells may be prokaryotic cells or eukaryotic cells. Vectors include, but are not limited to, plasmids, viruses, phage, transposons, YACs, and BACs.

Also provided are methods of obtaining expression of the variant polypeptides of DsRed by introducing the vectors and constructs comprising the disclosed variants into cells under conditions that permit expression of the variant polypeptide. The vector or construct may contain a polynucleotide encoding a variant polypeptide of DsRed linked to a polypeptide of interest as a fusion protein.

All references cited herein are incorporated by reference in their entireties. The following examples are meant only to be illustrative and are not meant as limitations on the scope of the invention or of the appended claims.

EXAMPLES

Example 1

Materials and Methods

The materials and methods described here were used throughout the following Examples unless otherwise indicated.

Expression Optimization

To screen for the optimal codon usage, all synonymous substitutions encoding residues 2-5 (Asp-Ser-Thr-Glu) were varied by annealing two sets of phosphorylated oligonucleotides (5'-CATGGAYTCNACNGARAACGT (SEQ ID NO:12)/5'-TYTCNGTNGARTC (SEQ ID NO:13) and (5'-CATGGAYAGYACNGARAACGT (SEQ ID NO:14)/5'-TYTCNGTNGARTC (SEQ ID NO:15)) subcloned into the DsRed.T3 gene using NcoI and AatII restriction sites. The mutant library was transformed into E. coli strain DH10B and ~4,000 colonies were screened using the previously described slide projector assay (Cronin and Hampton, 1999 Trends Cell Biol 9:36; Bevis and Glick, 2002 Nat Biotechnol 20:83-87). Briefly, fluorescence excitation was achieved by placing a 520+/−20 nm bandpass filter over the lens of a slide projector, and fluorescence emission was detected visually using laboratory goggles covered with a Kodak Wratten filter #22, which passes wavelengths>550 nm. Screening was performed in bacteria expressing the fluorescent proteins from a modified version of the pQE60 vector (Qiagen, USA) in which the hexahistidine tag coding region was removed in order to avoid any contribution of the tag to expression. The brightest clones were collected and sequenced.

To characterize expression, DsRed.T3 variants with sequences at codons 2-4 of GCC/TCC/TCC or GAC/AAC/ACC or GAT/AGC/ACT were transformed into DH10B cells carrying the pREP4 repressor plasmid (Qiagen). Cells were grown in Luria Broth (LB) to $OD_{600}$ of 0.5-0.6 and then induced with 1 mM isopropyl-β-D-thiogalactosidase (IPTG) for 2 h at 37° C. Translation was inhibited by addition of 30 μg/ml tetracycline and 170 μg/ml chloramphenicol and the proteins were chased for 6 h at 37° C. to allow for complete maturation. Cells density was normalized to $OD_{600}$ of 1.0 in LB and whole cell fluorescence was measured using a Tecan Safire II Microplate reader (Tecan Grp., Ltd.). Proteins were excited at 550±10 nm and emission was measured at 595±10 nm. Data were normalized to DsRed.T3. Controls for high expression from an exogenous start codon employed the pQE31 vector (Qiagen), which contains an N-terminal hexahistidine tag. Experiments were performed in triplicate.

To characterize protein expression, one $OD_{600}$ unit of each sample was centrifuged and resuspended in 400 μA SDS-polyacrylamide gel electrophoresis loading buffer, boiled for 10 minutes, and centrifuged again at 16,000×g for 5 minutes. 20 μl of supernatant was loaded per lane of an 8-12% polyacrylamide gel. As a control, 0-2 μg of purified hexahistidine-tagged DsRed.T3 was spiked into a lysate from cells containing an empty vector.

PISA Analysis

Crystal contacts in WT DsRed and DsRed.T4 crystal structures were examined using Protein interfaces, surfaces and assemblies service (PISA) at European Bioinformatics Institute (http://www.ebi.ac.uk/msd-sry/prot_int/pistart.html) to identify potential aggregation prone residues. Structures with the following PDB Ids were analyzed: 1GGX, 1G7K, 1ZGO, and 2VAE.

Mutagenic Library Construction and Screening

Combinatorial libraries for targeted aggregation and brightening screens were built using overlap-extension PCR (Ho et al., 1989 Gene 77:51-59) and DNA shuffling, using primers encoding the desired target substitutions. Error-prone PCR was used to generate libraries with random mutations (Cadwell and Joyce, 1995 in PCR Primer. A Laboratory Manual (eds. Dieffenbach and Dvekster) 583-589 Cold Spring Harbor Laboratory Press). The generated libraries were subcloned using NcoI/NotI into the modified version of pQE60 lacking an N-terminal hexahistine tag. For the aggregation studies, the mutant libraries were transformed into the *E. coli* strain DH5α. For the brightening screens, libraries were transformed into the *E. coli* strain DH10B.

To assay for decreased aggregation, bacterial colonies expressing DsRed variants were collected into 96-well round-bottom plates containing 175 μl Terrific Broth (TB) or LB. Cultures were grown for 2-4 hrs and induced with 2 mM IPTG for 6-12 hrs, centrifuged, and resuspended in 100 μl BPER II reagent (Pierce, Rockford, Ill.) for 15 min at 37° C. to lyse the cells. Lysates were centrifuged for 5 min at 5,000 rpm and the supernatants were transferred to black 96-well plates. The pellet was then resuspended in 100 μl BPER II and transferred to another black 96-well plate. Fluorescence in each fraction was measured on a Tecan Safire II Microplate reader with 550±10 nm excitation and emission at 595±10 nm emission. The percentage of total fluorescence in the pellet was determined. Approximately 2,000 colonies from the targeted mutants were screened. For the random screen, 30,000 colonies were pre-screened for fluorescence using the slide projector assay (see above) and approximately 3,000 of the fluorescent clones were screened for aggregation.

Screens for fluorescence brightness were carried out using the slide projector assay (see above). Approximately 60,000 colonies were screened from the targeted mutant library and approximately 120,000 colonies were screened from the random mutant library.

Purification and Spectral Analysis

Hexahistidine tagged DsRed variants were purified from bacteria as previously described. Briefly fluorescent proteins were expressed from the pQE81 vector (Qiagen). Plasmids were transformed into *E. coli* strain DH10B, grown in 50 ml cultures to $OD_{600}$~0.6, and induced with 1 mM IPTG for ~10 h. Cells were lysed in 2 ml BPER II for 15 min at 25° C. Protein was bound to $Ni^{2+}$-NTA agarose (Novagen), washed and eluted with 750 μl 0.3 M NaCl, 0.3 M imidazole-HCl, pH 7.4, and 0.1% sodium azide. Purified protein was then dialyzed against 50 mM HEPES, pH 7.4, 100 mM NaCl, and 1 mM EDTA in the dark.

Corrected excitation and emission spectra of DsRed variants were obtained on a Horiba Fluoromax-3 spectrofluorometer as previously described (Bevis and Glick, 2002 Nat biotechnol 20:83-87; Strongin et al., 2007 Protein Eng Des Sel 20:525-534). Molar extinction coefficients were determined at $Abs_{max}$ using a Spectronic Unicam GENESYS10 UV spectrophotometer. Protein concentrations were determined by amino acid analysis at the Molecular Structure Facility, University of California, Davis. Quantum yields were determined as described (Lakowicz, 1999 Principles of Fluorescence Spectroscopt $2^{nd}$ Ed Kluwer Academic New York; Baird et al., 2000 PNAS 97:11984-11989) using ethanolic rhodamine 101 as a reference. For quantum yield determination, excitation was at 535 nm and fluorescence emission was integrated from 550-800 nm.

Crystallographic Analysis

DsRed-Max hosted in a modified version of pQE31 encoding a TEV cleavage site between the start codon and hexahistine tag was expressed and purified as described above. After elution the protein sample was simultaneously buffer exchanged and concentrated to 12 mg/ml into 5 mM HEPES, pH 8.0, 100 mM NaCl, and 1 mM Tris(2-carboxyethyl)-phosphine hydrochloride (TCEP HCl) for crystallization trials using an Amicon Ultra centrifugal filter device (Millipore Corp., Billerica, Mass.). Protein crystals were grown at room temperature using the hanging drop method by mixing 2 μL1 reservoir solution with 2 μA sample.

Diffraction data were indexed using HKL2000, and molecular replacement was carried out using DsRed.T4 (PDB code 2VAE) as a search model in Phaser.

Photobleaching Experiments in *E. coli*

Photobleaching experiments were carried out using an AxioPlan 2 light microscope (Carl Zeiss, Inc) with a 100 W mercury arc lamp. Fluorescent proteins were bleached using a 40× (0.75 NA) objective and the Texas Red filter set (Chroma). Before bleaching, DH10B/pREP4 transformed with the fluorescent proteins were grown to an $OD_{600}$ of ~0.5 and induced with 2 mM IPTG. After a 2-h induction, translation was inhibited by addition of 30 μg/ml tetracycline and 170 μg/ml chloramphenicol and the proteins were chased for 4 h at 37° C. 1 OD unit of cells were then pelleted and resuspended in 500 μl 0.5% low-melt agarose in phosphate buffered saline (PBS), pre-warmed to 37° C. 1.5 μl of cell-agarose mixture were placed on a glass slide and coverslipped. Cells were continuously illuminated for 10 min and images were collected every 2 sec. Bleaching experiments were carried out in triplicate. Data were analyzed using Axio-Vision 4.6 software (Carl Zeiss, Inc).

Light-Induced Cell Death

To determine phototoxicity, *E. coli* strain DH10B was transformed with the pQE81 plasmid containing GFP or DsRed variants or a modified version of pQE60 with no hexahistidine tag and no insert. Cells were grown to an $OD_{600}$ of ~0.5 and induced with 2 mM IPTG for precisely 4 h. A $1:10^4$ dilution of each culture ($OD_{600}$~2.0) was made in LB immediately before light treatment yielding solutions with 150-200 cells/μl. For light treatment, a 2 μl drop of cells was added to a coverslip situated in a Petri dish assembly. This assembly included 2 wetted kimwipes to maintain humidity and a lid with a 3-4 mm diameter hole for the microscope objective. Light treated samples were exposed to 15 min of illumination from a 100 W mercury arc lamp passed through either the Texas Red, TRITC, or GFP filter and 5× (0.16 NA) objective on an AxioPlan 2 microscope. Untreated controls were placed on a coverslip in a second Petri dish assembly, but not exposed to fluorescence illumination.

Bacterial Cytotoxicity Assay

Fluorescent proteins in the modified pQE60 vector were transformed into *E. coli* strain DH10B and the cells were grown for 13 h at 37° C. To enhance colony color, the plates were stored at 4° C. for 2 days before the photo was taken.

Hematopoietic Stem and Progenitor Cell Growth Assay

This assay was carried out essentially as described (Tao et al. 2007 Stem Cells 25:670-678). Briefly, murine stem cell virus-based bicistronic retroviral constructs encoding EGFP, DsRed-Express, or DsRed-Express2 were transfected into the Phoenix-Eco packaging cell line to make ecotropic retroviral vectors. Low-density bone marrow mononuclear cells isolated from 8- to 12-week-old female C57BL/6J mice were cultured for 2 days with a cytokine cocktail (100 ng/ml murine stem cell factor, 100 ng/ml murine FLT3-ligand, and 100 ng/ml murine thrombopoietin) and then transduced with the retroviral vectors. At 87 h after transduction, the cells were sorted by flow cytometry. For each fluorescent protein, three wells with 20,000 fluorescent cells each were cultured in the presence of the cytokine cocktail. At selected time points, an aliquot from each well was analyzed by flow cytometry to determine total cell number and the percentage of fluorescent cells.

Example 2

Enhancement of Bacterial Expression

WT DsRed expresses poorly when translated from its endogenous start codon in prokaryotic cells. Previous work showed that mutating amino acids near the start codon could increase protein expression in bacteria. The S4T substitution was expanded upon to add A2D and S3N substitutions for maximal expression. However, the N3S reversion was selected in a screen to identify variants with increased solubility (see below).

In order to maintain both elevated protein expression due to suppression of mRNA secondary structure and protein solubility, a screen was performed in which all synonymous mutations were made in the codons corresponding to Asp2, Ser3, Thr4, and Glu5 in the fast maturing tetramer, DsRed.T3. Screening for the brightest variants using the slide projector assay as described above revealed the optimized sequence GAT/AGC/ACT/GAG (SEQ ID NO:16). To quantitate the observed increase in brightness, the fluorescence from bacterial cells expressing DsRed.T3, DsRed.T3-A2D/S3N/S4T (DsRed.T3-DNT), and DsRed.T3-A2D$^{GAT}$/Ser$^{AGC}$3/S4T$^{ACT}$ (DsRed.T3-DST) was measured. DsRed.T3-DST yielded slightly brighter fluorescence than DsRed.T3-DNT and a 15-fold increase in fluorescence relative to DsRed.T3 (FIG. 1A).

To demonstrate that the increase in fluorescence was due to increased protein expression rather than to a change in the intrinsic fluorescence of DsRed.T3, the DsRed protein concentration in the same samples used in the whole-cell fluorescence measurements was examined by Coomassie staining of an SDS-PAGE gel (FIG. 1B). As predicted, there is a large increase in the intensity of the band corresponding to DsRed, suggesting the 15-fold increased brightness observed with DsRed.T3-DST is due to increased protein expression relative to DsRed.T3.

Example 3

Modification of Surface Residues

Wild-type DsRed forms aggregates when expressed in cells. Eliminating a cluster of basic residues at the amino terminus decreased but did not eliminate this higher-order aggregation in the fast maturing tetramers. Recent work showed that expression of DsRed.T1 caused cytotoxicity in mouse hematopoietic stem cells (HSC). Because protein aggregation is thought to be responsible for several human diseases, we reasoned that the cytotoxicity in HSC might be the result of DsRed.T1 aggregation. We therefore modified the surface of the fast maturing tetramers to eliminate higher order aggregation. Both site-directed and random mutagenesis were performed and mutant variants were screened with a quantitative assay to measure aggregation.

Figure 2:
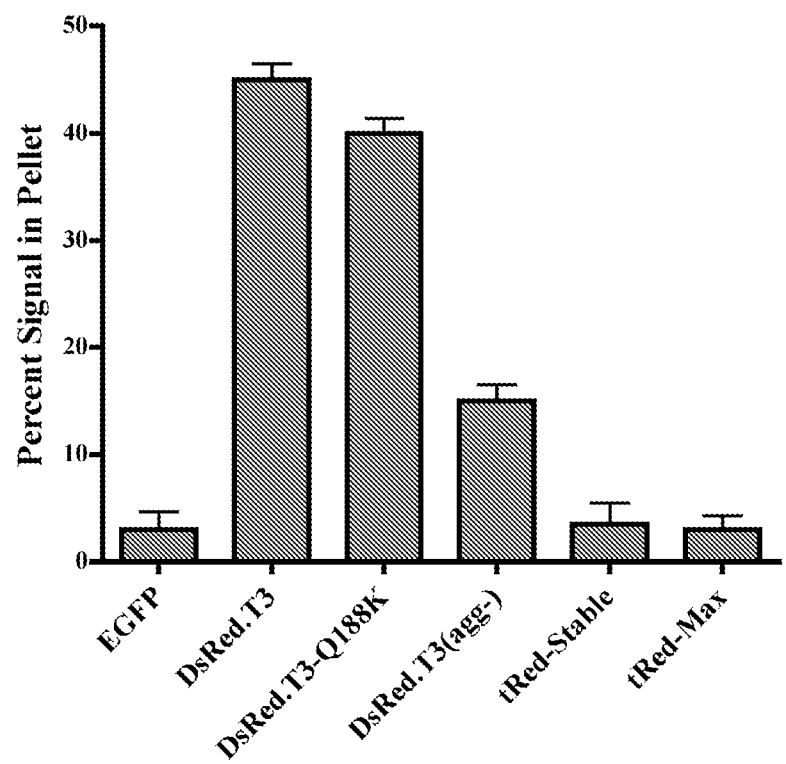
FIG. 2 is a bar graph of an aggregation assay comparing EGFP and several DsRed variants.

This "aggregation assay" is a modification of the one used by Bevis and Glick (2002 Nat Biotechnol 20:83-87) to reduce higher order aggregation during the engineering of the fast-maturing variants. Briefly, bacterial cells grown in 96-well plates were made to over-express a fluorescent protein. These cells were then lysed, separated into supernatant and pellet fractions, and fluorescence associated with each fraction was determined. Aggregating fluorescent proteins associate with the pellet. A detailed description of this assay as well as details of the screens described below can be found in Example 1. Using this assay, 45% of the DsRed.T3 fluorescence was in the pellet, whereas EGFP has only 3-6% of its fluorescence in the pellet (FIG. 2).

Engineering of DsRed-Express2

DsRed-Express was modified in an effort to reduce the higher-order aggregation (DsRed.T1). As a preliminary step, amino acids 2-4 were modified to boost expression in *E. coli* (see above). Ten additional substitutions were introduced to stabilize the protein and eliminate potentially interactive surface residues (Table 1). The Round 1 variant showed a small but reproducible decrease in aggregation in the bacterial extraction assay.

TABLE 1

Substitutions made during the creation of DsRed-Express2 and DsRed-Max[a]

| Construct | Residues differing from DsRed.T3 |
|---|---|
| Round 1 | A2D, S3N, S4T, D6N, R36K, K47Q, C117T, K121H, M141L, K168E, D169G, I210V, G219A, L225Q |
| Round 2 | A2D, S3N, S4T, D6N, E10P, R17H, R36K, K47Q, C117T, K121H, M141L, K168E, D169G, Q188K, I210V, G219A, L225Q |
| Round 3 | A2D, S4T, D6N, E10P, R17H, R36K, K47Q, C117T, K121H, M141L, D169G, Q188K, I210V, G219A, L225Q |
| DsRed-Express2 | A2D, S4T, D6N, E10P, R17H, R36K, K47Q, C117T, K121H, M141L, D169G, Q188K, I210V, T217A, G219A, L225Q |
| DsRed-Max | A2D, S4T, D6N, E10P, R17H, R36K, K47Q, Q66M, V73T, C117T, K121H, M141L, D169G, V175C, Q188K, I210V, G219A, L225Q |

TABLE 1-continued

Substitutions made during the creation of DsRed-Express2 and DsRed-Max[a]

| Construct | Residues differing from DsRed-Express |
|---|---|
| DsRed-Express2 | A2D, S4T, D6N, E10P, R17H, R36K, K47Q, S117T, K121H, M141L, A145P, D169G, Q188K, I210V, G219A, L225Q |
| DsRed-Max | A2D, S4T, D6N, E10P, R17H, R36K, K47Q, Q66M, V73T, S117T, K121H, M141L, A145P, D169G, V175C, Q188K, I210V, A217T, G219A, L225Q |

[a]The initial optimization started with DsRed.T3 rather than DsRed-Express because DsRed.T3 is the brightest of the rapidly maturing DsRed tetramers. Based on subsequent analysis, we mutated the interior of the improved protein to match that of DsRed-Express.

To identify additional residues that promote aggregation, we reasoned that inter-tetramer interactions might be visible in the high-concentration environment of a protein crystal. Packing interactions in published DsRed crystal structures (See Strongin et al. 2007 Protein Eng Des Sel 20:525-534) were analyzed with the Protein Interfaces, Surfaces and Assemblies (PISA) server as described above. Certain residues were consistently found to make inter-tetramer contacts. An example of a candidate residue is Gln188, which makes a symmetric hydrogen bond to the Gly155 backbone on the contacting molecule. If a lysine were substituted at position 188, the crystal contact might then be disrupted by a charge-charge-repulsion. Sixteen residues identified using PISA (Table 2) were mutagenized combinatorially with Round 1 as the template. The substitutions E10P, R17H, and Q188K reduced aggregation. These three substitutions were combined to create the Round 2 variant, which had ~15% of its fluorescence in the pellet.

TABLE 2

Residues targeted from crystal packing analysis

| Residue | Wild-type amino acid | Other amino acids tested[a] | DsRed-Express2 amino acid |
|---|---|---|---|
| 9 | K | A | K |
| 10 | E | P | P |
| 13 | R | Q | R |
| 17 | R | H, Y | H |
| 29[b] | I | V | I |
| 58[b] | W | F, Y | W |
| 77 | A | E | A |
| 85 | L | Q | L |
| 115 | D | G | D |
| 116 | G | D | G |
| 166 | K | E, L, T | K |
| 188 | Q | E, K | K |
| 198 | K | E, S, T | K |
| 203 | S | K, E, D | S |
| 206 | E | A, S | E |
| 209 | T | S | T |

[a]The amino acids tested were chosen based on the physical properties of the side chains and homology alignments with other fluorescent proteins. The wild-type residue was also tested in all cases.
[b]Residues 29 and 58 are internal, but seem to be important for creating a prominent cleft in the protein.

Figure 3:
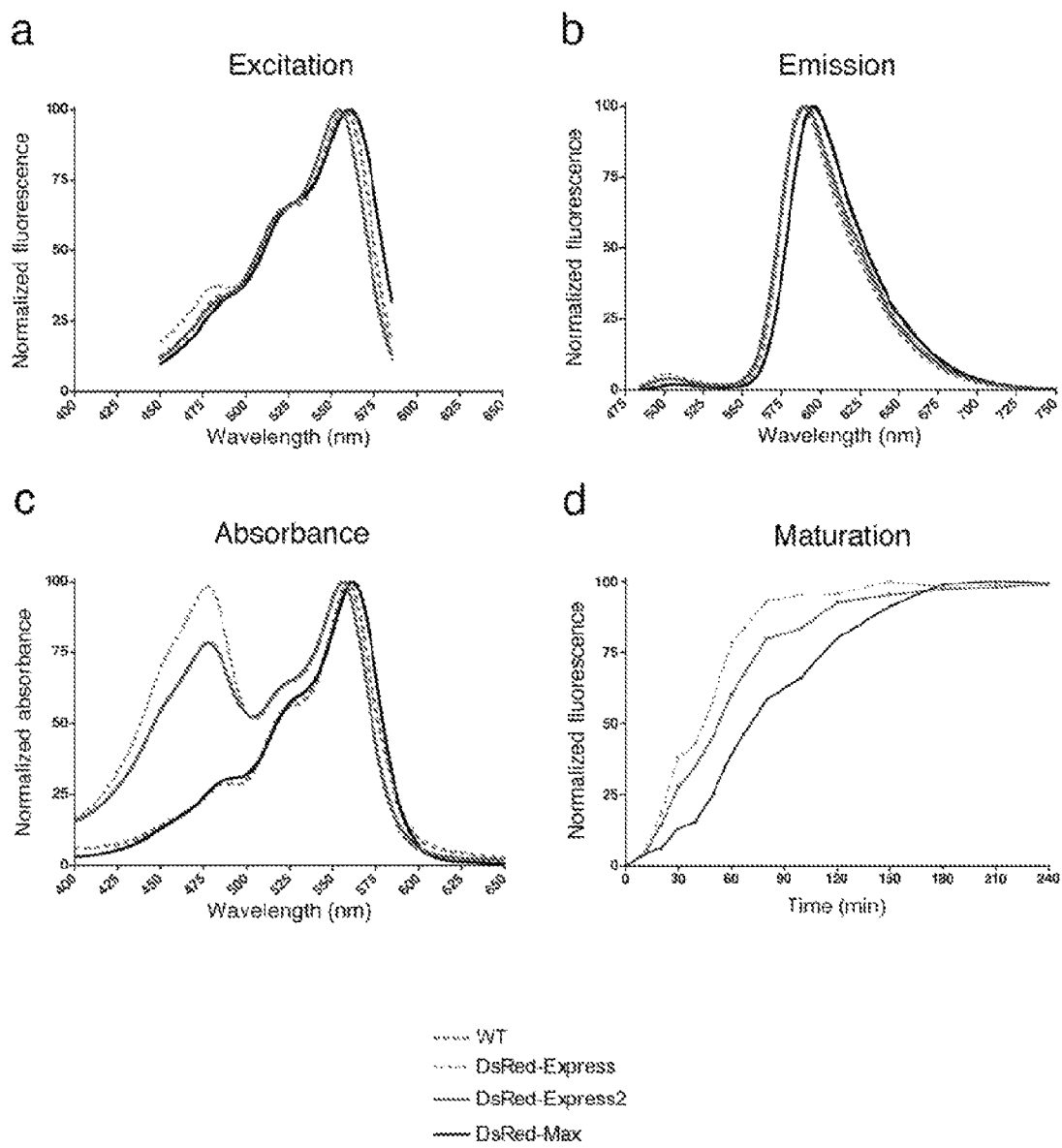
FIG. 3 is set of graphs showing the excitation, emission, absorbance spectra and maturation kinetics for the DsRed tetramers.

Round 2 was then subjected to random mutagenesis followed by screening with the bacterial extraction assay. This screen led to the substitutions N3S and E168K, both of which reverted mutations that had been introduced into Round 1. The resulting variant was termed DsRed-Express2. Compared to DsRed-Express, DsRed-Express2 showed almost identical brightness and photostability, marginally slower maturation, and less contaminating blue absorbance and green emission (Table 3, FIGS. 3 and 4).

TABLE 3

Properties of red fluorescent proteins

| Variant | Excitation/Emission maxima | Extinction coefficient | Quantum yield | Relative brightness[a] | Maturation half-time (h) | Photobleaching half-time (s)[b] |
|---|---|---|---|---|---|---|
| Wild-type DsRed[c] | 558/583 | 51,500 | 0.71 | 1 | 11 | — |
| DsRed-Express | 554/586 | 33,800 | 0.44 | 0.41 | 0.6 | 71 ± 3 |
| TurboRFP[d] | 550/573 | — | — | — | 1.5 | 32 ± 1 |
| Katushka | 584/631 | 76,300 | 0.32 | 0.67 | 0.6 | 15 ± 1 |
| RFP611 | 555/606 | 109,700 | 0.6 | 1.8 | 2.7 | 7 ± 2 |
| DsRed-Monomer[e] | 557/592 | 27,300 | 0.14 | 0.10 | 1.3 | 15 ± 1 |
| mCherry[f] | 585/609 | 66,400 | 0.23 | 0.42 | 0.6 | 18 ± 1 |
| tdTomato[f] | 553/581 | 85,700 | 0.69 | 1.6 | 2.0 | 5 ± 1 |
| TagRFP | 554/582 | 77,000 | 0.47 | 0.98 | 1.5 | 8 ± 4 |
| TagRFP-S158T | 554/584 | 67,800 | 0.40 | 0.73 | 1.6 | 20 ± 2 |
| mKate | 584/632 | 45,500 | 0.33 | 0.41 | 1.3 | 15 ± 2 |
| mKO2 | 549/563 | 54,300 | 0.82 | 1.2 | 1.8 | 5 ± 1 |
| DsRed-Express2 | 554/591 | 35,600 | 0.42 | 0.41 | 0.7 | 64 ± 4 |
| DsRed-Max | 560/589 | 48,000 | 0.41 | 0.54 | 1.2 | 9 ± 1 |

Unless otherwise indicated, all measurements were obtained during the present study using standardized procedures.
[a]Brightness was calculated as the product of extinction coefficient and quantum yield, and was normalized to a value of 1 for wild-type DsRed.
[b]Photobleaching half-times during widefield illumination are listed as mean ± s.e.m. for three independent experiments.

TABLE 3-continued

Properties of red fluorescent proteins

| Variant | Excitation/Emission maxima | Extinction coefficient | Quantum yield | Relative brightness[a] | Maturation half-time (h) | Photobleaching half-time (s)[b] |
|---|---|---|---|---|---|---|

[c]The maturation rate of wild-type DsRed was taken from Bevis and Glick 2002 Nat Biotechnol 20: 83-87. Photobleaching of wild-type DsRed in vivo could not be reliably measured due to slow maturation.
[d]Because TurboRFP showed very poor solubility during extraction from bacteria, we were unable to perform brightness measurements for this protein.
[e]For DsRed-Monomer, all of the data except the photobleaching half-time were taken from Strongin et al. 2007 Protein Eng Des Sel 20: 525-534.
[f]The initial report describing mCherry and tdTomato listed substantially faster maturation rates (Shaner et al. 2005 Nat Biotechnol 22: 1567-1572. Our measurement for mCherry is more consistent with a subsequent paper (Merzylak et al. 2007 nat Methods 4: 555-557.

Example 4

Modification of Chromophore Facing Residues

Figure 4:
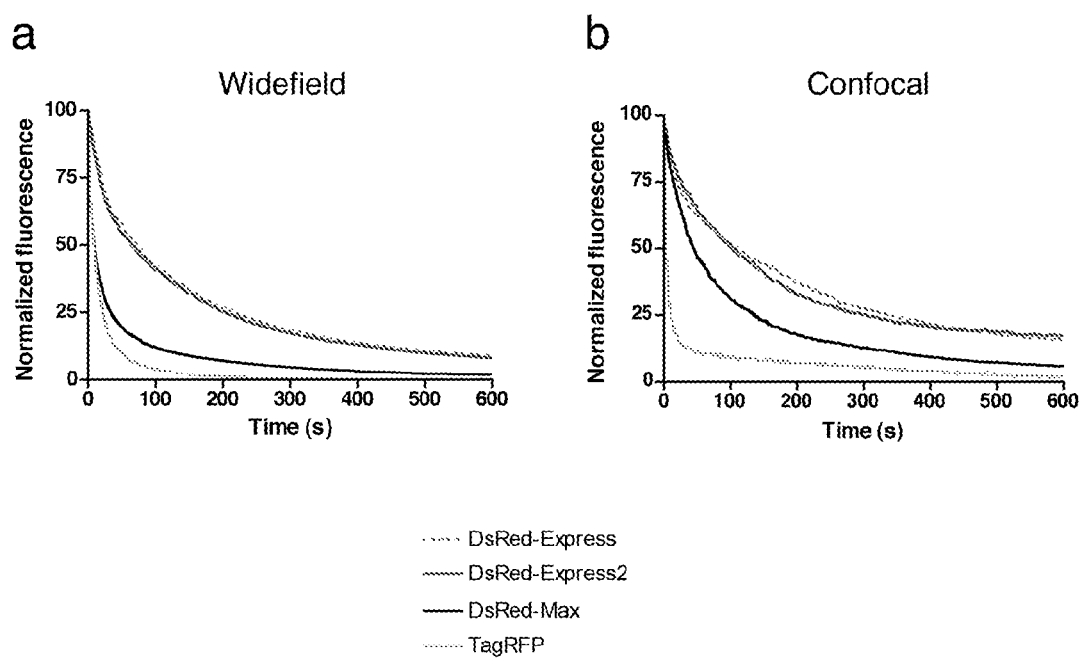
FIG. 4 is a set of graphs showing the photobleaching kinetics of the DsRed tetramers using a widefield microscope with a Texas Red filter (535-585 nm) and confocal microscope with a 543 excitation laser.

DsRed-Express2 is less bright than wild-type DsRed (Table 3). The Q66M substitution has been shown to decrease or eliminate the proportion of chromophores exhibiting 480 nm absorbance and/or green fluorescence. This "green" chromophore species has been estimated to represent 40-60% of the WT DsRed chromophores and that percentage is increased in the fast-maturing variants. Therefore, introduction of the Q66M substitution increases the molar extinction coefficient by increasing the proportion of 558 nm absorbing "red" chromophores. Targeted mutagenesis of key residues led to the brighter variant DsRed-Max, which contained the substitutions Q66M, V73T, and V175C. Unfortunately, the Q66M substitution rendered DsRed-Max much less photostable than DsRed-Express2 during widefield imaging, although this problem was less pronounced during confocal imaging (Table 3 and FIG. 4). DsRed-Max is vividly colored, making it useful as a marker for directly visualizing labeled cells. DsRed-Max is an optimized DsRed.T3 variant containing the expression and solubility optimizing substitutions (Ala2Asp$^{GAT}$, Ser3Ser$^{AGC}$, Ser4Thr$^{ACT}$, Glu10Pro, Arg17His, Gln188Lys) and brightness optimized substitutions (Gln66Met, Val73Thr, Val175Cys) (Table 1). DsRed-Max, is ~30% brighter than DsRed-Express2. Compared to DsRed-Express2, DsRed-Max has even lower green emission (FIG. 3), but is slower to mature and more photolabile (FIG. 4 and Table 3). DsRed-Max should be useful when brightness and/or pure red emission are of paramount importance.

Example 5

Crystallization of DsRed-Max

A DsRed variant with reduced aggregation might be expected to show fewer crystal contacts. This prediction was confirmed by solving a crystal structure of DsRed-Max to 2.4 Å resolution (Table 4). When compared to the previously analyzed crystals of wild-type DsRed and DsRed.T4, the DsRed-Max crystal showed a higher solvent content and about a 50% decrease in surface area of inter-tetramer contacts (Table 5). Table 6 shows the amino acid substitutions in DsRed-Max and DsRed-Express2.

TABLE 4

Data collection and refinement statistics for DsRed-Max

| Data collection | |
|---|---|
| Space group | $P2_12_12$ |
| Unit cell dimensions | a = 115.5, b = 122.6, c = 164.9 Å |
| | $\alpha = \beta = \gamma = 90.0°$ |
| Molecules per asymmetric unit | 8 |
| X-ray source | APS 14-BM-C |
| Wavelength (Å) | 0.900 |
| Resolution range (Å) | 50-2.40 (2.49-2.40) |
| Total/unique observations | 597,626/91,172 |
| Completeness (%) | 98.0 (84.8)[a] |
| <I/sig I> | 14.3 (2.2) |
| Rsym (%) | 14.2 (61.4) |
| Refinement and model statistics | |
| Rcryst (%) | 22.3 |
| Rfree (%) | 27.1 |
| Non-hydrogen atoms (solvent) | 14,710 (491) |
| Average B-factor (Å$^2$) | 35.3 |
| RMS Bond lengths (Å) | 0.011 |
| RMS Bond angles (°) | 1.4 |

[a]Values in parentheses are for the high-resolution shell.

TABLE 5

Protein crystal statistics for DsRed tetramers

| Protein (PDB code) | Solvent content (%) | Buried surface area (Å$^2$)[a] |
|---|---|---|
| Wild-type DsRed (1ZGO) | 35 | 4,900 |
| Wild-type DsRed (1G7K) | 39 | 2,900 |
| Wild-type DsRed (1GGX) | 38 | 3,500 |
| DsRed.T4 (2VAE) | 47 | 3,400b |
| DsRed-Max (2V4E) | 58 | 1,700 b |

[a]For a given tetramer, the total buried surface area of inter-tetramer interfaces was calculated from PISA analysis as the sum of all packing interfaces larger than 100 Å$^2$. Intra-tetramer interfaces were excluded.
[b]The average buried surface area per tetramer is listed for structures with two tetramers per asymmetric unit.

TABLE 6

Amino acid substitutions in the new tetrameric variants

| Position | DsRed.T3 | DsRed-Max | DsRed-Express2 |
|---|---|---|---|
| 2 | Ala | Asp$^{GAT}$ | Asp$^{GAT}$ |
| 3 | Ser$^{TCC}$ | Ser$^{AGC}$ | Ser$^{AGC}$ |
| 4 | Ser | Thr$^{ACT}$ | Thr$^{ACT}$ |
| 6 | Asp | Asn | Asn |
| 10 | Glu | Pro | Pro |
| 17 | Arg | His | His |
| 36 | Arg | Lys | Lys |
| 47 | Lys | Gln | Gln |
| 66 | Gln | Met | Gln |
| 73 | Val | Thr | Val |
| 117 | Cys | Thr | Thr |
| 121 | Lys | His | His |
| 141 | Met | Leu | Leu |
| 169 | Asp | Gly | Gly |
| 175 | Val | Cys | Val |

TABLE 6-continued

Amino acid substitutions in the new tetrameric variants

| Position | DsRed.T3 | DsRed-Max | DsRed-Express2 |
|---|---|---|---|
| 188 | Gln | Lys | Lys |
| 210 | Ile | Val | Val |
| 217 | Thr | Thr | Ala |
| 219 | Gly | Ala | Ala |
| 225 | Leu | Gln | Gln |

The amino acids present at potentially substituted positions are listed for DsRed-Max and DsRed-Express2. Substitutions relative to DsRed.T3 are highlighted in bold. Superscripts following an amino acid indicate the codon used if different than the Clontech, human optimized codon.

Example 6

Cytotoxicity in Bacteria

Figure 5:
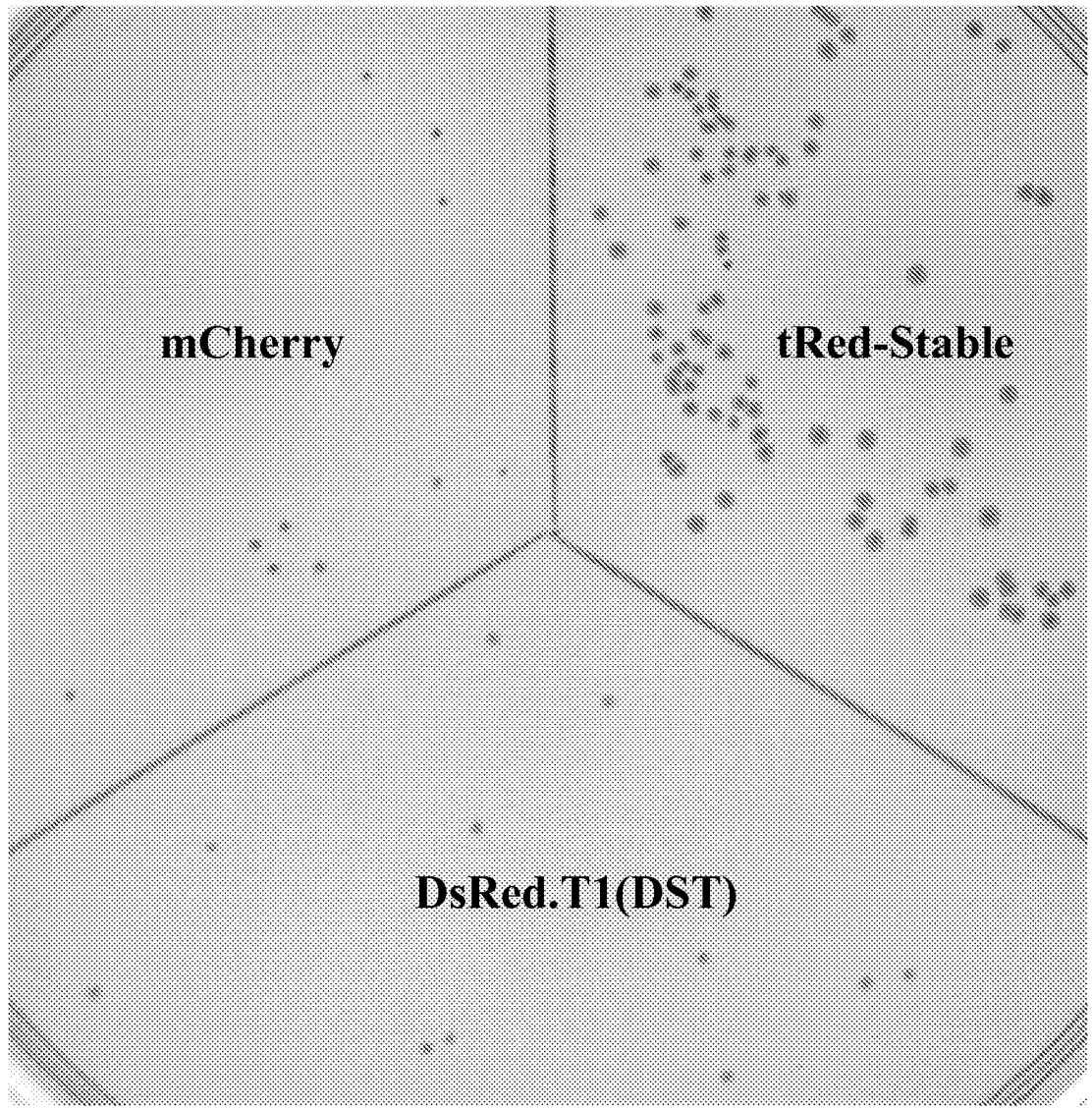
FIG. 5 is a photograph of bacterial colonies expressing various DsRed variants.

The surface of the fast-maturing DsRed tetramers was modified in an attempt to decrease the toxicity of these proteins to cells. To test the hypothesis that the new variants with increased solubility are also less cytotoxic, DsRed.T1 modified with DST to normalize expression, the monomeric DsRed variant called mCherry (Shaner et al., 2005 Nat Biotechnol 22: 1567-1572), and DsRed-Express2 (tRed-Stable) were constitutively over-expressed in *E. coli* and the colony sizes of these strains were compared (FIG. 5). Bacteria expressing DsRed-Express2 had the largest colonies suggesting that DsRed-Express2 exhibited the least cytotoxicity. Bacterial cells expressing DsRed-Max had the same sized colonies as those expressing DsRed-Express2.

Example 7

HeLa Cell Cytotoxicity and Growth Assays

Figure 6:
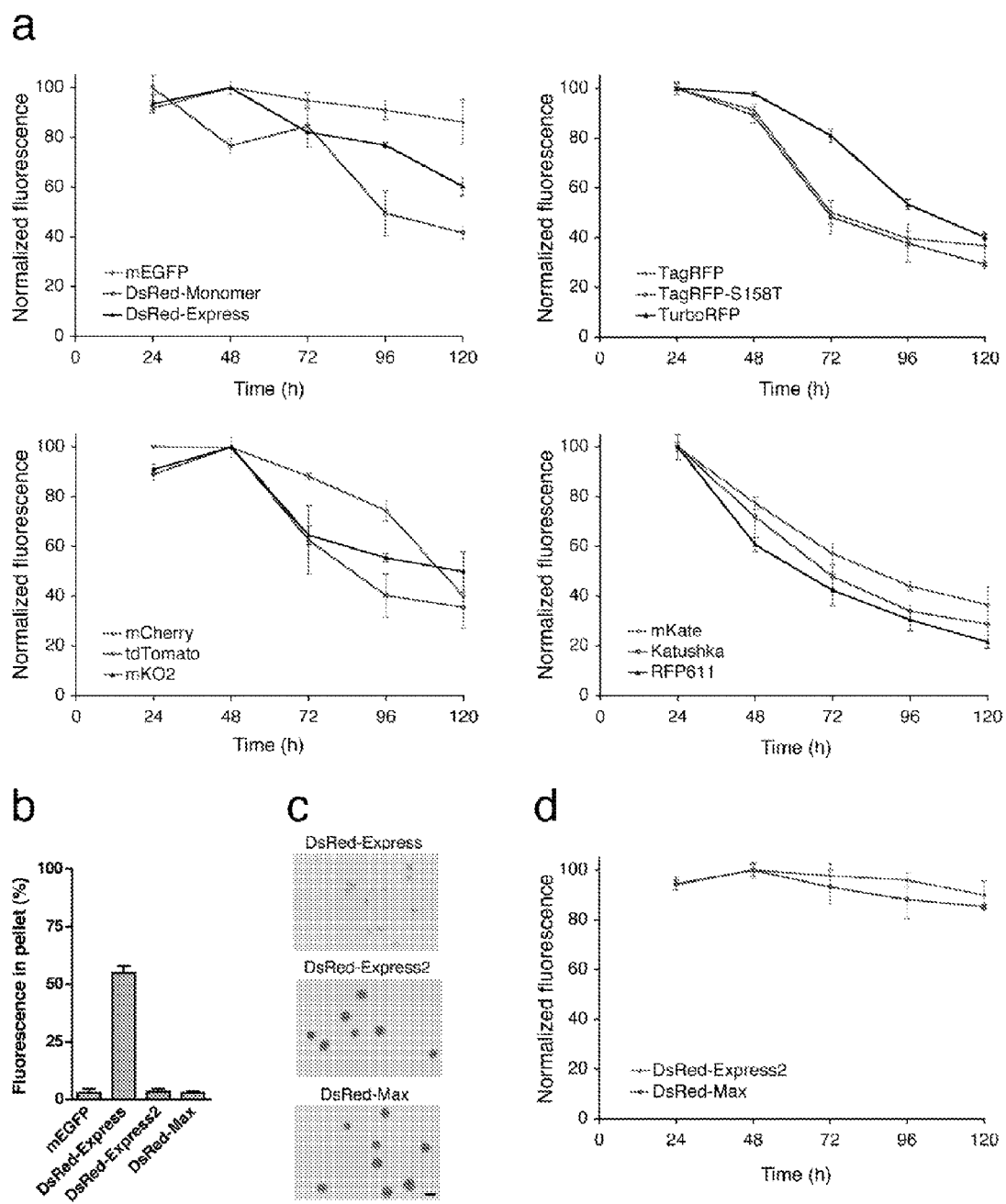
FIG. 6a is a set of graphs showing the cytotoxicity in HeLa cells associated with constitutive high level expression of the indicated fluorescent proteins. Cells were harvested and fluorescence measured by FACS daily, the strongest signal obtained for a given protein was defined as 100 units.
FIG. 6b is a bar graph showing the percentage of the fluorescent protein found in the pellet of a bacterial lysate.
FIG. 6c is a set of photographs showing that DsRedExpress2 and DsRed-Max are minimally cyctotoxic to the bacterial cells.
FIG. 6d is a graph like that in FIG. 15a showing the relative amount of fluorescent protein expression over time in transiently transfected HeLa cells.
Figure 7:
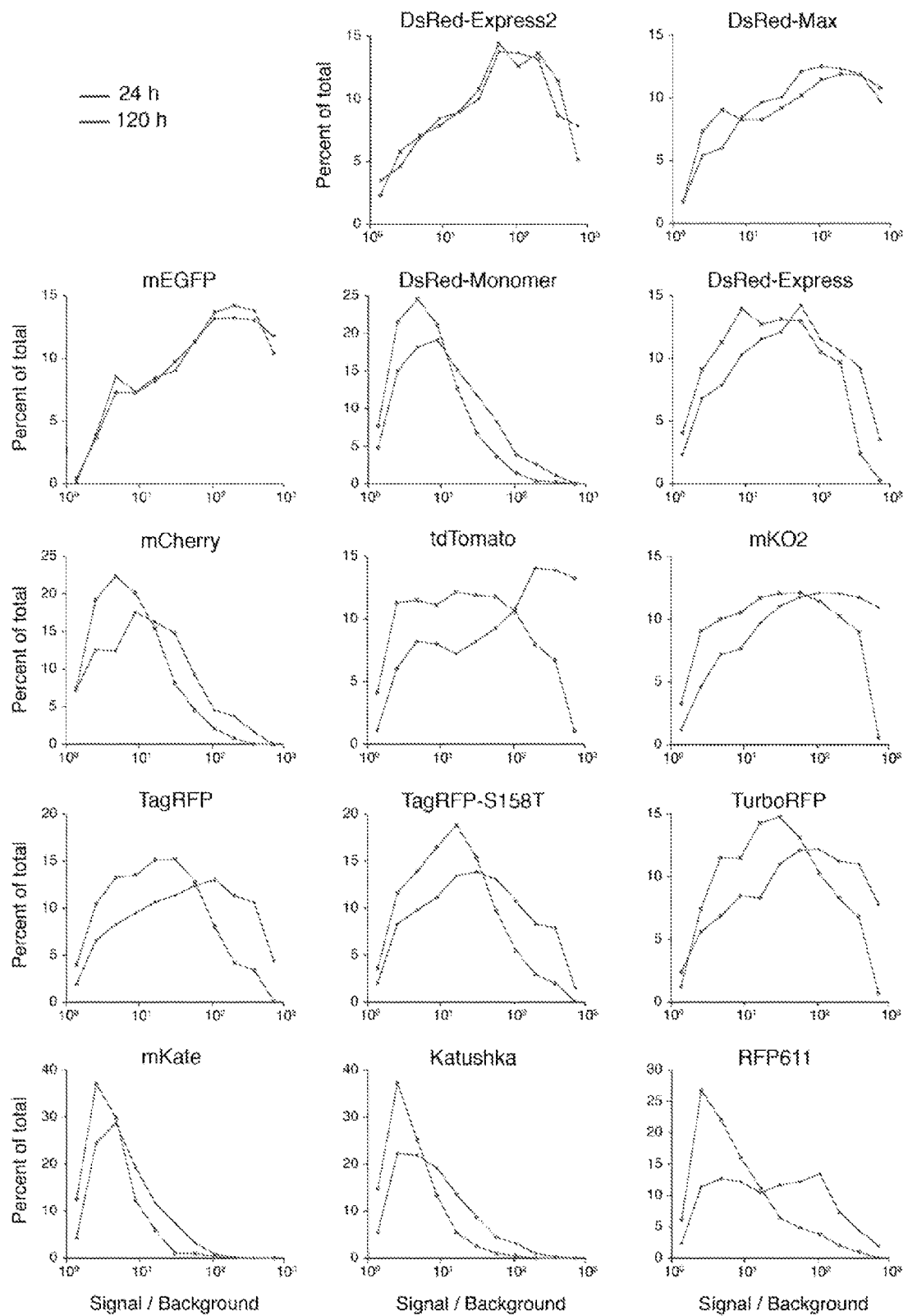
FIG. 7 is a set of graphs showing the fluorescence intensity distributions of HeLa cells transiently transfected with the indicated fluorescent proteins.

To assess cytotoxicity in HeLa cells, we expressed fluorescent proteins by transient transfection with a standard plasmid containing the strong CMV promoter. Viable fluorescent cells were analyzed by flow cytometry at daily intervals after transfection. For mEGFP, average cellular fluorescence remained nearly constant from 24 h to 120 h (FIG. 6a). By contrast, all of the red fluorescent proteins showed progressive declines in average fluorescence (FIG. 6a) due to preferential loss of the most highly expressing cells (FIG. 7). Expression of red fluorescent proteins caused many cells to detach from the growth surface, further indicating cytotoxicity.

For transient transfection assays, the fluorescent protein genes were subcloned into pDsRed1-N1 (Clontech). Identical wells of HeLa cells at ~50% confluence were transfected using Lipofectamine 2000 (Invitrogen). At intervals of 24 h after transfection, three wells for each fluorescent protein were analyzed with an LSR II flow cytometer (BD Biosciences), using either a 488-nm laser for mEGFP or a 543-nm laser for the red fluorescent proteins. Between 20-50% of the viable cells were detectably fluorescent at 24 h after transfection. Data were processed using FlowJo software (Treestar Inc.).

For lentiviral expression assays, HeLa cells expressing the desired fluorescent protein were generated by lentiviral gene transfer using the Lenti-X HT Packaging System with associated vectors (Clontech). A fluorescent protein gene with a Kozak sequence upstream of the start codon was subcloned into pLVX-DsRed-Monomer between BamHI and NotI. pLVX-Puro was used as a no-insert control. To generate viral particles, HEK 293T/17 cells (ATCC No. CRL-11268) in a 10-cm dish at 50% confluence were transfected with ~6 µg of the appropriate vector. Viral particles were collected 48-72 h post-transfection and frozen in aliquots at −80° C. Viral particle concentration was determined using the QuickTiter Lentivirus Quantitation Kit (Cell Biolabs). HeLa cells at 50% confluence in a 10-cm dish were transduced by adding 3.5× $10^{10}$ viral particles to the medium together with polybrene (4 µg/ml final concentration). The medium was changed after 24 h, and cells were grown in the absence of drug selection. Viable fluorescent cells were analyzed at 3 or 10 days post-transduction using an LSR II flow cytometer (BD Biosciences) with 488-nm excitation and a FITC (525/15 nm) filter (green fluorescence) or 543-nm excitation and a PE (585/15 nm) filter (red fluorescence).

To measure the growth of cells expressing a given fluorescent protein after lentiviral transduction, 3000 fluorescent HeLa cells were cultured in each of 12 wells in a 96-well plate. On Days 1, 2, 3, and 4, cells from three wells were trypsinized and counted with a hemocytometer. As a control, viable cells were cultured and counted after transduction with lentiviral particles generated using pLVX-Puro.

Transiently transfected HeLa cells expressing DsRed-Express2 or DsRed-Max maintained nearly constant average fluorescence (FIG. 6d), and the highly expressing cells remained viable (FIG. 7). Thus, with both bacterial and mammalian plasmid expression vectors, DsRed-Express2 and DsRed-Max are tolerated better than any of the other red fluorescent proteins tested.

Example 8

Retroviral Transduction

Figure 8:
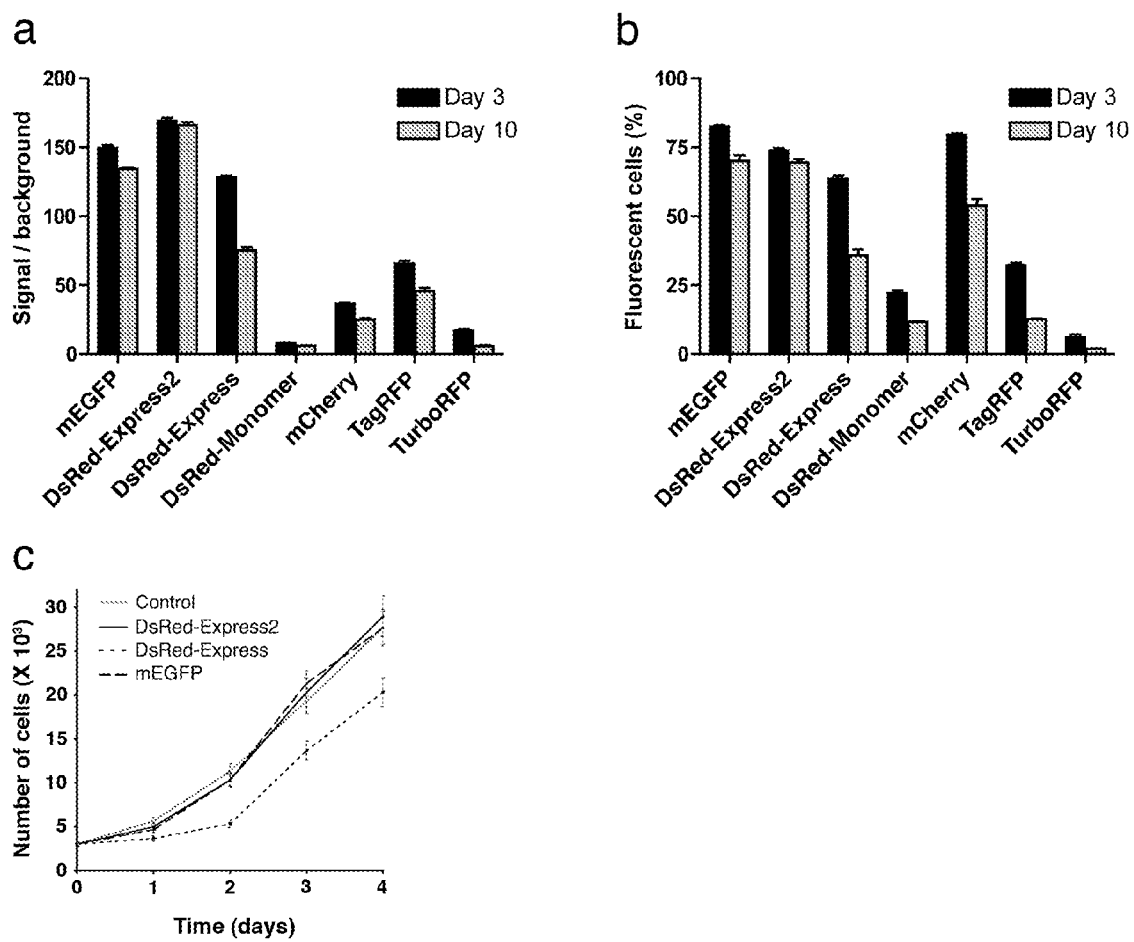

For mammalian cells, an alternative to plasmid-based expression is retroviral transduction, which yields long-term expression at moderately high levels. We used a commercial lentiviral system to compare DsRed-Express2 with five other red fluorescent proteins plus mEGFP. HeLa cells were transduced using the same lentiviral titer for each fluorescent protein, and then viable fluorescent cells were analyzed by flow cytometry after 3 or 10 days. At Day 3, the fluorescence signal over background was stronger for DsRed-Express2 than for any other red fluorescent protein (FIG. 8a). At Day 10, the average fluorescence intensity was nearly unchanged for mEGFP and DsRed-Express2, but had dropped substantially for the other fluorescent proteins, presumably due to loss of the most highly expressing cells. This interpretation was supported by counting the percentage of viable cells that were fluorescent. Between Day 3 and Day 10, this percentage was nearly unchanged for mEGFP and DsRed-Express2, but dropped substantially for the other fluorescent proteins (FIG. 8b). Even at Day 3, relatively few fluorescent cells were observed with DsRed-Monomer, TagRFP, and TurboRFP, possibly reflecting cytotoxicity at early stages of expression. In a separate experiment, lentivirally transduced HeLa cells containing DsRed-Express showed a lag in growth compared to cells containing DsRed-Express2 or mEGFP (FIG. 8c). Our data confirm that with standard cell culture expression vectors, fluorescent protein cytotoxicity is an important problem that can be overcome by using DsRed-Express2.

Example 9

Cytotoxicity in Murine Hematopoietic Stem Cells (HSC)

In a previous report murine HSC expressing EGFP or DsRed.T1 were transplanted into mice, and while EGFP expressing cells continued to grow over time, the DsRed.T1 expressing cells were lost from the population. Similarly, when a mixed population of HSC expressing EGFP or DsRed.T1 were co-plated and challenged in an in vitro competition assay under culture conditions promoting the preservation and growth of stem and primitive progenitor cells, EGFP positive cells grew robustly while DsRed.T1 expressing cells did not.

Figure 9:
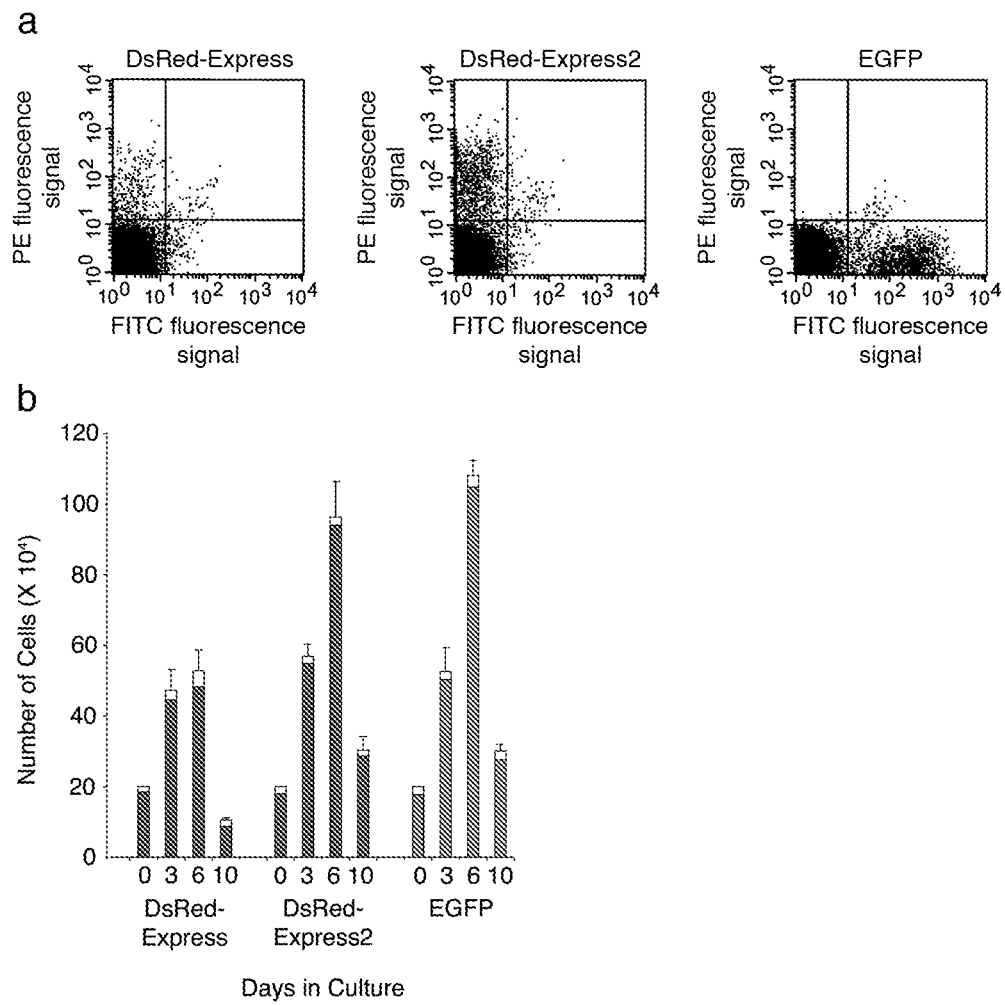
FIG. 9a is a set of flow cytometry graphs of mononuclear bone marrow derived cells retrovirally transduced with vectors comprising the indicated proteins and sorted after 87 hours.
FIG. 9b is a graph depicting the number of transduced cells which are fluorescent over time in culture (shaded portion of bar) and the number of transduced cells which are not fluorescent (white portion of bar). The decrease in total cell number at day 10 is not fluorescent protein-related, but reflects senescence that is routinely observed under in vitro conditions.

Here, murine bone marrow cells were retrovirally transduced with DsRed-Express, DsRed-Express2, or EGFP. Viable fluorescent cells were collected by flow cytometry at 87 h post-transduction (Day 0), and then individual cultures were started with 20,000 cells. For each culture we recorded the total cell number and the number of fluorescent cells after 3, 6, and 10 days. At Day 0, the cells containing DsRed-Express2 were more abundant, and were on average twice as bright as those containing DsRed-Express (FIG. 9a). The cells containing DsRed-Express2 proliferated to the same degree as those containing EGFP, but the cells containing DsRed-Express proliferated much less (FIG. 9b). These data are similar to the results with HeLa cells. We conclude that DsRed-Express2 is minimally cytotoxic in a variety of cell types.

Example 10

Phototoxicity

Figure 10:
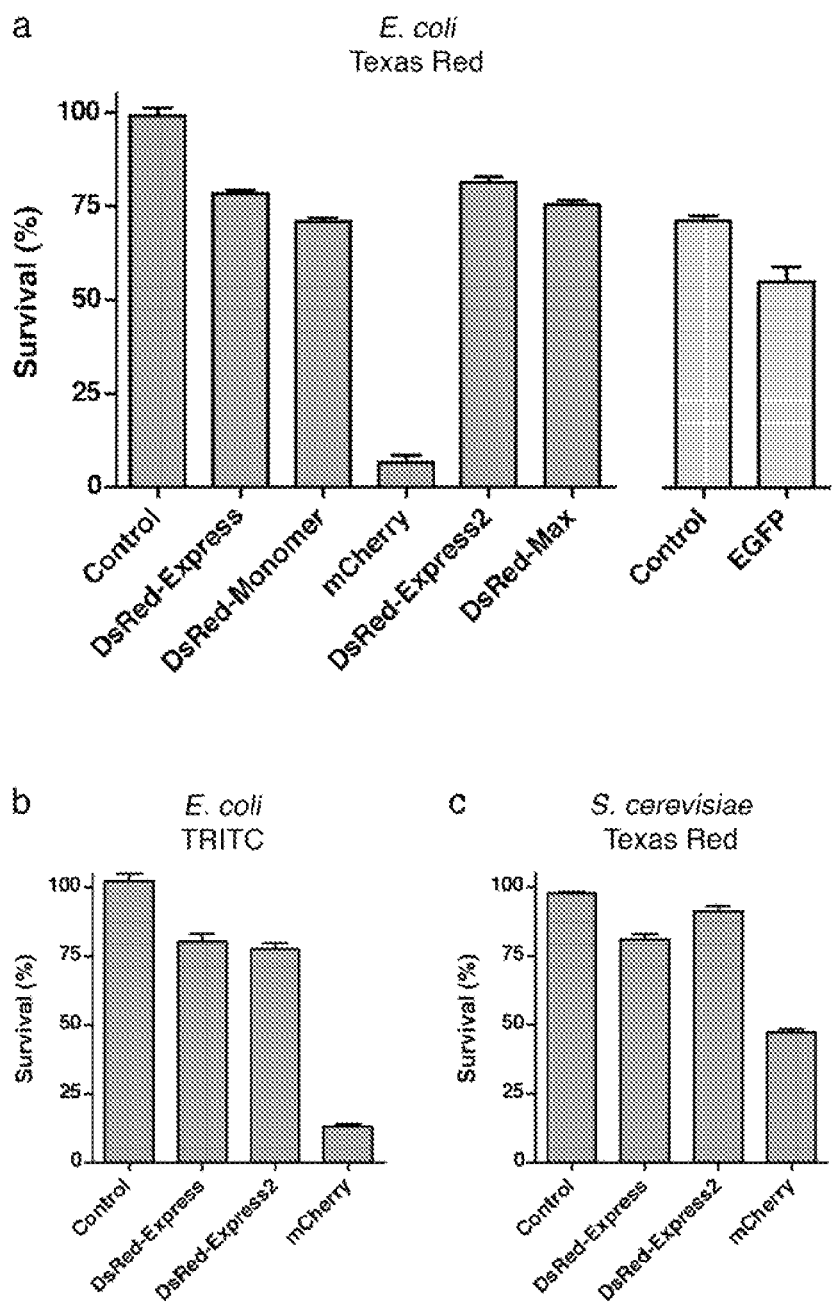
FIG. 10a is a bar graph showing E. coli cells expressing no fluorescent protein or the indicated fluorescent protein illuminated through a Texas Red (535-585 nm) filter gray bars or a GFP (470-510 nm) filter (light gray bars) for 15 minutes. Parallel samples were treated identically but not illuminated. Cells were plated and grown overnight. The graphs shows the percent survival calculated by the number of colonies from the illuminated sample divided by the number from the non-illuminated sample.
FIG. 10b is a bar graph showing the same type of assay as in FIG. 10a with the TRITC (530-560 nm) filter used.
FIG. 10c is a bar graph showing the same type of assay as in FIG. 10a, but S. cerevisiae cells and a nuclear targeted fluorescent protein were used. The cells were only illuminated with a Texas Red filter for 10 minutes in this assay. Percent survival was calculate after two days of growth.

Excitation of fluorescent proteins in vivo can cause phototoxicity. To quantify this effect, E. coli cells expressing a fluorescent protein were illuminated for 15 min with an epifluorescence microscope using a low-power objective, and the percent survival was measured relative to a non-illuminated sample. When the excitation light was passed through a Texas Red (535-585 nm) filter, no phototoxicity was seen with control cells containing an empty vector, but some cytotoxicity was seen with DsRed-Express (78% survival), DsRed-Monomer (71% survival), DsRed-Express2 (81% survival), and DsRed-Max (75% survival) (FIG. 10a). A direct comparison with green fluorescent proteins is difficult, but the phototoxicity of variants such as DsRed-Express2 appears to be similar to that of EGFP (FIG. 10a). mCherry was considerably more phototoxic (7% survival). The greater phototoxicity of mCherry was not due to higher protein expression, nor was it due to stronger excitation because similar results were obtained with a TRITC (530-560 nm) filter (FIG. 10b), which should give more efficient excitation of the non-red-shifted DsRed variants than of the red-shifted mCherry.

To test phototoxicity in a eukaryotic system, we labeled the yeast Saccharomyces cerevisiae by using the constitutive TPI1 promoter to drive expression of nuclear-localized DsRed-Express, or DsRed-Express2, or mCherry. Nuclear localization enhanced fluorescent protein phototoxicity, presumably by facilitating DNA damage. Relatively low phototoxicity was seen with DsRed-Express (81% survival) and DsRed-Express2 (91% survival), whereas mCherry showed higher phototoxicity (47% survival) (FIG. 10c). The combined data imply that phototoxicity is of practical importance and that DsRed-Express2 is a good choice in this regard.

Example 11

Homology Guided Mutagenesis

We devised a method to efficiently screen amino acid variation at several positions, which we term homology guided mutagenesis. The principle of this method is that if all 20 amino acids were screened in combination at multiple positions, the mutagenic library would be too diverse to comprehensively screen. If however the number of amino acids at each of those multiple positions were reduced, the mutagenic library could be comprehensively screened. We reduce the diversity at any given position by only including those amino acids that are favored in the evolutionary history of fluorescent proteins, i.e. DsRed homologues. We therefore assume that the evolutionary process has eliminated unfavorable amino acid substitutions and retained those substitutions that are either neutral or beneficial. Generally the homology guided mutagenesis strategy presents a diversity of 2-5 amino acids at a given position eliminating the need to screen 20 amino acids at every position.

Example 12

Brightening DsRed.M1

The initial goal was to make DsRed.M1 brighter by increasing the molar extinction coefficient and quantum yield. The homology guided approach was used and several screens performed with the goal of further stabilizing the surface of DsRed.M1 and introducing novel intramolecular interactions. These screens divided the surface of DsRed into distinct regions of adjacent residues and introduced variability at those positions with only limited overlap between the regions. For instance the "surface cluster #1" screen targeted Lys158, Ser162, Asp176, and Lys178. The "surface cluster #2" screen targeted Glu30, Glu32, Lys45, and Gln47. The "charge cluster" screen also targeted Glu30, but in combination with Gln13, Arg17, and Lys121. The "loops" screen targeted Asp115, Gly116, and Met141, Lys168, and Asp169. To address the question of whether the DsRed had been over mutagenized, a "reversion" screen was performed to test reversions at many of the positions mutated in earlier screens, including some positions leading to DsRed.M1.

Application of the homology guided approach reduced the diversity present in these mutagenic libraries substantially. For example, the "surface cluster #1" screen had the most complexity of the above screens with 576 possible combinations in the mutagenic library. However, if the four targeted residues had been randomized there would have been 160,000 possible combinations. To screen a 576 combination library with five-fold over-sampling, two Petri plates with approximately 2,000 bacterial colonies each needed to be screened using the slide projector assay. It took five to ten minutes to screen these plates. By contrast, a 160,000 combination library with the same degree of over-sampling would require at least 30 hours to screen 400 Petri plates.

The above screens as well as many subsequent attempts at combining their various substitutions resulted in a variant called DsRed.M1*, which contains additional amino acid substitutions as follows: D6N, K121H, M141L, K168E, and D169G. Interestingly, the "reversion" screen indicated that none of the substitutions tested should be reverted to their WT amino acid.

Example 13

The Funnel Screen

Figure 11:
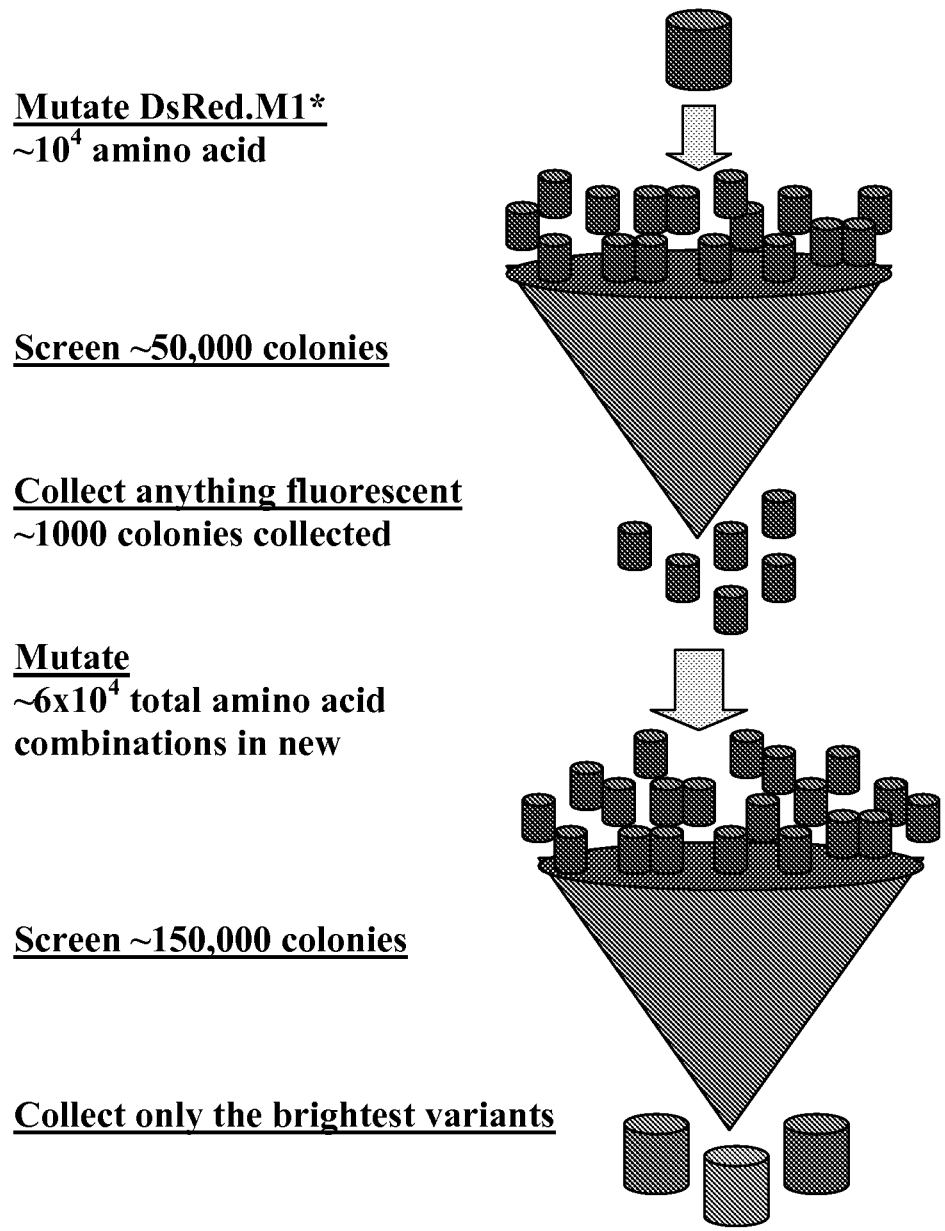
FIG. 11 is a schematic depiction of the funnel screening assay.

Fourteen residues surrounding the chromophore were mutated in combination with one another in an attempt to significantly increase brightness in a single step. Once again, the homology guided approach was essential. Randomization of each of the fourteen positions would result in $1.6 \times 10^{18}$ combinations in the library, but because we minimized the library using homology as a guide there were only $3 \times 10^6$ combinations. Unfortunately though, $3 \times 10^6$ combinations were still too many to screen, so another trick was needed to make the screen possible. The solution was to do the screen in two parts. In the first half of the screen, approximately half of the positions were mutated. Instead of applying a stringent selection, all colonies that exhibited any fluorescence were selected into the wells of a 96-well plate. Those cells were grown to saturation, and DNA was prepared from a mixture of each well. This first round library then became the template for the second half of the screen in which the remaining residues were mutated. The second round variants were also screened with the slide projector assay and a stringent selection was applied to choose the brightest clones (FIG. 11). Because this screen collects the diversity from a large library and funnels it into reasonably sized groupings, it was named the "funnel" screen. The variants collected from the first round screen all retained some fluorescence and those that did not fluoresce at all were not collected. Therefore, one caveat to the "funnel" screen is that it assumes the evolutionary path towards "ultimate" brightness always goes through a fluorescent intermediate. Based on our experience, we believe this to be a reasonable assumption. Further, dim variants were collected, so although we assume that there is never a non-fluorescent intermediate, we did not assume that each evolutionary step improves brightness.

In the first half of the screen Ala44, Ser62, Gln66, Met83, His163, Ser197, Leu199, Gln213, and Ala217 were mutated. The library had a diversity of 10,368 combinations. Approximately 50,000 colonies were screened with the slide projector assay and 1,000 clones were collected, representing approximately 2% of the library, into the 96-well plates. This library was used as the template into which mutations at Phe91, Gln109, Phe124, Leu150, and Phe177 were added. The combined diversity was then 288 new combinations added to the approximately 200 combinations in the first round library for a total diversity of approximately 60,000 combinations in the second round. We screened 150,000 colonies from that library and selected the 59 brightest, which were then re-screened. Finally, the 14 brightest colonies were selected and sequenced (FIG. 11).

Figure 12:
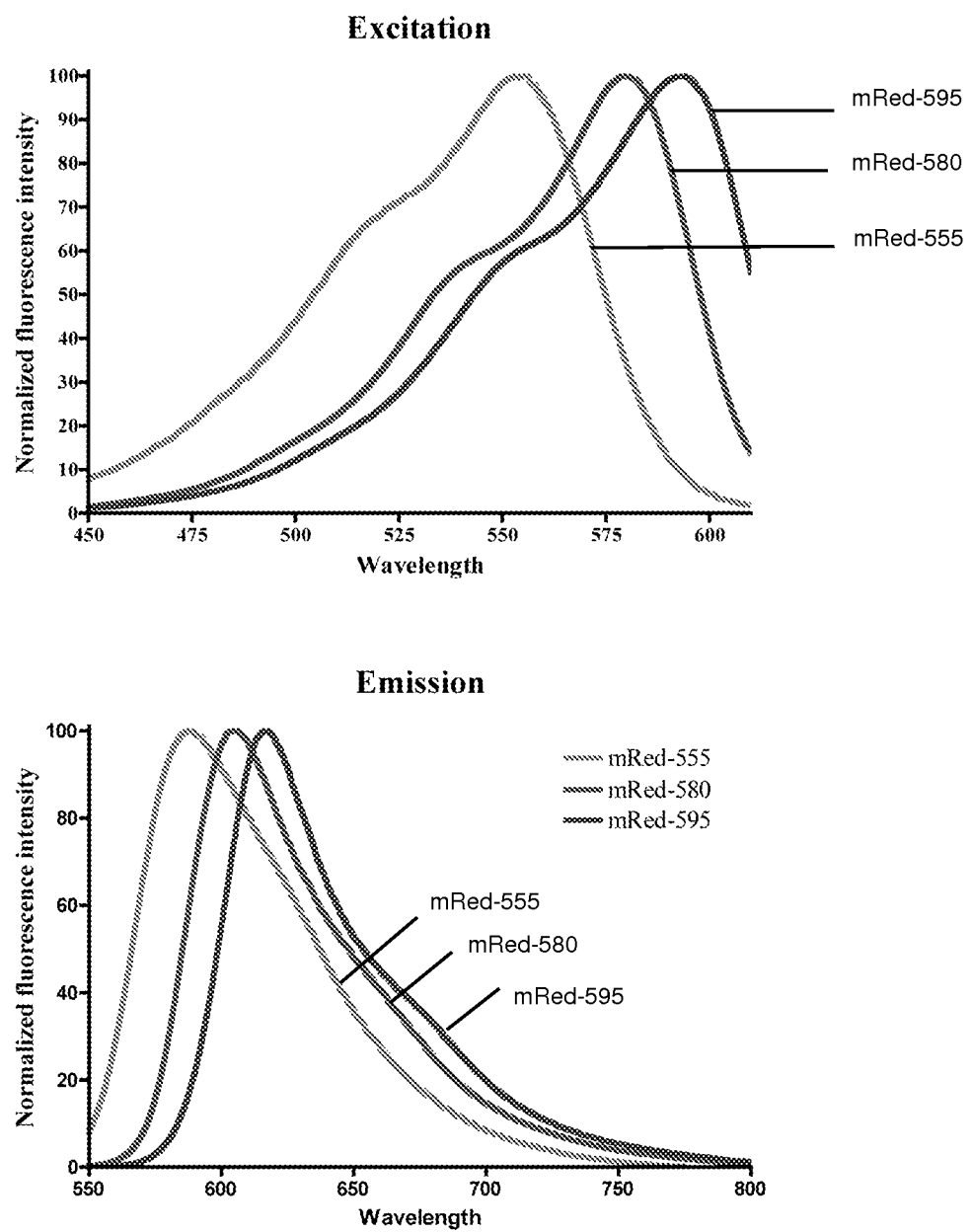
FIG. 12 is a set of line graphs showing the excitation and emission spectra for mRed-555, mRed-580 and mRed-595.

During the screening process many of the colonies exhibited a much deeper red fluorescence than usual, so these were collected and purified. These colonies contained DsRed variants with far-red fluorescence spectra and were therefore an important discovery. A bright far-red fluorescent protein is highly desirable because of further decreased light scattering in tissues and even lower phototoxicity compared to red fluorescent proteins (Shcherbo et al. 2007 Nat Methods 4: 741-746). We therefore used the far-red color variant as the base construct for further mutagenesis including solubility optimization (see below). However, proteins with DsRed-like spectra are also desirable because their spectra align well with common laser lines and because they can be FRET acceptors for GFP. In order to create an optimized variant with DsRed-like excitation and emission spectra, we mutagenized the optimized far-red variant and screened for new variants with wild-type like spectra. During the funnel screen we also identified a variant with spectra intermediate between WT-DsRed and the far red variant. These color variants with greatly improved brightness compared to DsRed.M1 were named mRed-xxx where xxx represents the approximate excitation maximum in nanometers, e.g. mRed-555, mRed-580 and mRed-595. mRed-555 is twice as bright as DsRed.M1. Both mRed-580 and mRed-595 are four times as bright as DsRed.M1, and better than mCherry (FIG. 12/Table 7).

mRed-595 was further enhanced to create mRed(sol)-595 (below), and blue shifted to create mRed(sol)-560 (below).

mRed-595 contains the following brightening and spectral shifting substitutions relative to DsRed.M1: D6N, R17Y, A44V, Q66M, M83F, D115G, G116D, K121H, A141L, L150M, H163M, K168E, D169G, T174N, F177V, S197I, N203S, and A217S (Table 7).

mRed-580 contains the following brightening and spectral shifting substitutions relative to DsRed.M1: D6N, R17Y, Q66M, M83L, D115G, G116D, K121H, F124V, A141L, L150M, H163M, K168E, D169G, T174N, F177V, S197I, N203S, and Q213L (Table 7).

mRed-555 contains the following brightening substitutions relative to DsRed.M1: D6N, R17Y, Q66M, M83L, D115G, G116D, K121H, M141L, K168E, D169G, N203S and A217S. His163 was substituted with methionine in many of the isolates but ultimately His 163 remained unchanged in mRed-555 (Table 7).

TABLE 7

Amino acid substitutions in the mRed variants

| Residue | DsRed.M1 | mRed-555 | mRed-580 | mRed-595 |
|---|---|---|---|---|
| 6 | Asp | Asn | Asn | Asn |
| 17 | Arg | Tyr | Tyr | Tyr |
| 44 | Ala | Ala | Ala | Val |
| 66 | Gln | Met | Met | Met |
| 83 | Met | Leu | Leu | Phe |
| 115 | Asp | Gly | Gly | Gly |
| 116 | Gly | Asp | Asp | Asp |
| 121 | Lys | His | His | His |
| 124 | Phe | Phe | Val | Phe |
| 141 | Ala | Leu | Leu | Leu |
| 150 | Leu | Leu | Met | Met |
| 163 | His | His | Met | Met |
| 168 | Lys | Glu | Glu | Glu |
| 169 | Asp | Gly | Gly | Gly |
| 174 | Thr | Asn | Asn | Asn |
| 177 | Phe | Phe | Val | Val |
| 197 | Ser | Ser | Ile | Ile |
| 203 | Asn | Ser | Ser | Ser |
| 213 | Gln | Gln | Leu | Gln |
| 217 | Ala | Ser | Ala | Ser |

The amino acids present at potentially substituted positions are listed for mRed-555, mRed-580, and mRed-595. Substitutions relative to DsRed.M1 are highlighted in bold.

TABLE 8

Summary of mRed spectral and biophysical properties

| Protein | Excitation Max (nm) | Emission Max (nm) | Molar Extinction Coefficient | Quantum Yield | Relative Brightness |
|---|---|---|---|---|---|
| WT DsRed | 558 | 583 | 58,000 | 0.68 | 1.00 |
| DsRed.M1 | 559 | 592 | 25,200 | 0.17 | 0.11 |
| mRed-555 | 554 | 588 | 73,700 | 0.12 | 0.22 |
| mRed-580 | 580 | 605 | 48,800 | 0.36 | 0.44 |
| mRed-595 | 594 | 617 | 52,200 | 0.31 | 0.41 |

Example 14

Effects of Select Substitutions

The Q66M mutation eliminates most of the green chromophore species and thereby increases the molar extinction coefficient. Interestingly, the F177V substitution reintroduces this green species. However, the F177V substitution also increases the quantum yield. The increase in quantum yield is greater than the decrease in molar extinction coefficient, so F177V contributes a net increase to brightness.

Q213L is another interesting substitution which is only present in mRed-580. When this residue is reverted to leucine, the mRed-580 spectra red-shift. In other words, this is a blue shifting substitution. We and others have identified very few blue-shifting substitutions in DsRed and it is potentially interesting because there is no fast maturing and photostable, true orange monmeric fluorescent protein. Y193H was identified during the development of DsRed.M1 because it brightened and blue shifted variants with K83M. However, it seems that this effect can be better described as a suppression of the K83M red-shift, because it does not cause a blue shift in other backgrounds (not shown). A44V and F124L are additional differences between mRed-580 and mRed-595. A44V is assumed to contribute to the red shift seen in mRed-595. Reverting Leu124 to phenylalanine in mRed-580 resulted in less brightness but no color shift.

The M66T substitution creates a significant blue-shift rendering the far-red protein red-orange. This likely occurs because through the formation of a second heterocycle formed in the chromophore between the hydroxyl of the Thr66 sidechain and the carbonyl carbon of Thr66. This chemistry has been observed in crystal structures of mOrange and OFP from *Corynactis californica*. Similarly the lysine sidechain at position 66 in zFP538 forms a second heterocycle. In the above examples formation of a second heterocycle prevents formation of the DsRed acylimine and thus restricts electron delocalization and the resulting red-shift. Substitution of position 66 with a threonine represents a novel strategy to create a red fluorescent protein from a far-red fluorescent protein.

Large hydrophobic amino acids at position 83 seem to greatly stabilize the DsRed monomers. K83M was crucial for developing DsRed.M1 and all of the current monomers still require a hydrophobic amino acid at that position for fluorescence. It seems that the larger the sidechain, the more stable the protein. Upon alkaline lysis of bacterial cultures expressing mRed-595 (containing M83F) for minipreps, there is a spectral shift (from purple to cherry red) but most of the color remains through the first several steps of the miniprep procedure, indicating that mRed-595 is not denatured to the same extent as other fluorescent proteins. Just like the original K83M substitution, K83F containing mRed-595 confers improved tolerance for other substitutions. However, a hydrophobic residue at position 83 causes Lys70 to swing away from the chromophore and therefore decreases quantum yield. Position 73 faces Lys70 and substitutions at those positions may exert their brightening effects by repositioning Lys70 over the chromophore. The substitutions V73A, V73T, H75C, H75K, and H75R also increase brightness likely through a similar mechanism, and these may be incorporated into any variant including mRed-595, mRed(sol)-595, and mRed(sol)-560.

Finally, position 217 is a serine in mRed-595 and mRed(sol)-560 but it is an alanine in mRed-580. It is likely that position 213, which is a leucine only in mRed-580, influences the nearby position 217, so mRed-580 differs from the other two mRed variants. Thr217Ala is a maturation-enhancing but brightness-decreasing substitution in the tetramers, and the optimal amino acid for that position is context dependent and variable among alanine, serine, and threonine.

Example 15

Reducing Aggregation in mRed Variants

The problem of higher order aggregation in DsRed is not limited to tetrameric variants. When present at high local concentrations, monomeric DsRed variants also tend to aggregate. This phenotype has been observed by our lab when DsRed.M1 is fused to the yeast transmembrane Golgi SNARE protein, Gos1. It has also been seen by many other labs when DsRed.M1 and/or mCherry are fused to proteins including a yeast amino acid transporter called Can1, and the mammalian proteins ERGIC-53, VSV-G, integrins, actin, and caveolin. Surprisingly when the exact same fusions are made to GFP instead of the red monomers, they "work". Because the above proteins are all present at high local concentrations in cells, it is reasonable to assume that the artifacts seen with fusions to red fluorescent proteins are the result of concentration dependent higher order aggregation. Further, these problems are seen both with our monomers and more commonly with mCherry. It should also be noted that GFP is a weak dimer (Kd of approximately 100 µM) and will self-associate at high local concentrations in cells. For example, GFP has been shown to drive proteins into plasma membrane microdomains or to rearrange endomembranes. However, addition of a monomerizing mutation abrogates these artifacts. Thus, proteins do achieve high local concentrations, and the fusion tag that is added to a native protein can significantly impact localization if it has a tendency to self-associate.

The residues involved in aggregation in the DsRed tetramer (described above) are solvent exposed, so those same residues are solvent exposed in the monomer. The surface substitutions incorporated in the tRed variants thus became the starting point for improving the aggregation properties of the mRed variants. Unfortunately however, the bacterial aggregation assay employed for the tetramer is not a viable assay for the monomers because they are comparably soluble to monomeric GFP even though the red monomers and monomeric GFP behave differently in cells.

Figure 13:
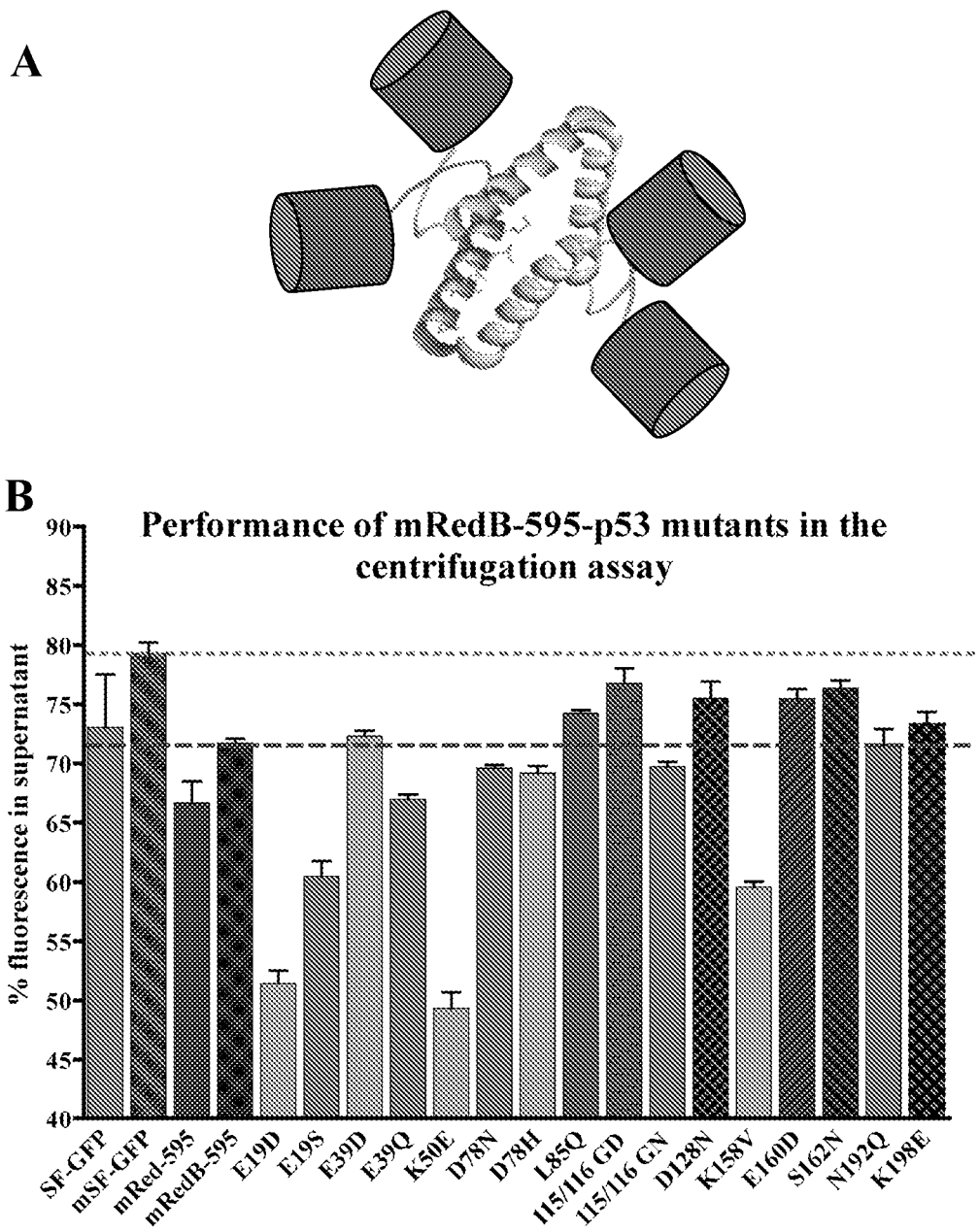
FIG. 13a is a schematic of the predicted structure of artificially tetramerized monomeric DsRed proteins.
FIG. 13b is a bar graph showing the results of the monomeric protein aggregation assays.

We needed either to devise a new assay or modify the existing assay so that the dynamic range would be sufficient to assay DsRed monomers. Any interactive surface on a tetramer is tetravalent simply because of the quaternary structure of the molecule. Perhaps the reason the original assay worked is that the tetravalent tetramer is better able to cross-link into insoluble aggregates than the monovalent monomer. It would follow then, that if the monomer were re-tetramerized with some artificial tetramerization domain, the aggregation assay might be made to work with DsRed monomers. To test this hypothesis we fused the GCN4-LI coiled-coil domain or the p53 transcription factor tetramerization domain to GFP, monomeric GFP, and various mRed variants (e.g. FIG. 13A). These tetramerization domains are small, fewer than 30 amino acids, and have been used previously to tetramerize heterologous proteins. As predicted, re-tetramerizing mReds or GFP brought the solubilities into a range where changes could be detected by the assay. Furthermore, GFP and monomeric GFP could be distinguished from one another (FIG. 13B). As a technical note, there was poor fluorescent protein expression when the tetramerization domains were fused to EGFP but robust expression when they were fused to a recently described GFP variant called Superfolder GFP (SF-GFP), which folds better in bacteria. Expression was not a problem with the mRed variants. Both GCN4-LI and p53 gave similar results, but because there is an antibody available for p53 and because the data were more consistent with p53, we moved forward with that domain.

Example 16

Identifying Aggregation Prone Residues

Once we had an assay, the next step was to identify residues that could be targets for mutagenesis. We chose to use mRed-595 as the template for further mutagenesis and not the other color variants because (1) proceeding with multiple variants lowers speed and efficiency, (2) mRed-595 and its derivatives are the most stable mRed variants, (3) if any one of the mRed variants were to make a substantial impact on the biomedical research community, it would be the far-red mRed-595, and (4) any additional surface substitutions identified could be incorporated into the other color variants at a later time.

DsRed has a unique structural feature in that two of the β-sheets composing the 11-stranded β-barrel partially splay apart to form what is referred to as "the canyon." The edges of β-sheets are often "sticky" so closing the canyon might reduce aggregation. There is a tryptophan residue (Trp58) positioned on the central β-helix that appears to be holding the canyon open. We fixed Trp58 as a smaller tyrosine or phenylalanine and then mutated surrounding residues to identify substitutions that could pair with the substitutions at position 58. Using the slide projector assay we identified the combination Trp58Tyr and Ile29Val as improving brightness and likely closing the canyon. We have been unable to crystallize a variant with the Trp58Tyr and Ile29Val substitutions, so it is not clear if the canyon was in fact closed. Regardless, this combination of substitutions increases brightness and is likely to decrease aggregation.

All of the solubility enhancing surface substitutions present in the tRed variants were introduced into the mRed-595. This includes the following substitutions: A2D$^{GAT}$, S$^{TCC}$3S$^{AGC}$, S4T$^{ACT}$ (see above for codon optimization), E10P, Y17H, G115D, D116G, E168K, and Q188K (Table 9). Note that the substitutions at Asn3, Gly115, Asp116, and Glu168 are reversions to the WT residue. The substituted mRed variant was named mRedB-595. mRedB-595 is several percent more soluble than mRed-595 when each is fused to the p53 tetramerization domain (FIG. 13B). Thus the modified aggregation assay can identify changes in mRed variants, and knowledge from mutagenesis of the tetramer can inform mutagenesis of the monomer.

Despite the increased solubility in mRedB-595, it is not as soluble as monomeric SF-GFP. The DsRed.M1 crystal structure was examined using PISA and a similar analysis to the one used for DsRed tetramers (see above) was performed. PISA demonstrated that Asp115 sits in a pocket on the adjoining monomer, but Gly116 points away from this pocket. Positions 115/116 are typically as Gly/Asp or Gly/Asn in the homologues, so the screen we performed included D115G and G116D or G116N (see below). A manual inspection of DsRed.M1 to identify candidate residues was also performed. These analyses collectively suggested: Glu19, Glu39, Lys50, Asp78, Leu85, Asp115, Gly116, Asp128, Lys158, Glu160, Ser162, Asn192, and Lys198 as the best candidates for mutagenesis. Homology was used as a guide to choose which amino acids to sample. Because the number of samples was small, each substitution was performed individually rather than as a screen, and then solubility was assessed using the modified aggregation assay (FIG. 13B).

Several substitutions resulted in increased solubility and increased brightness, notably: L85Q, DS115G/G116D, D128N, E160D, S162N, and K198E (FIG. 13B, Table 9; mRedx-595). Interestingly, when all of these substitutions are combined into a single variant, solubility actually decreased. Because the greatest single improvement came from the Asp115Gly/Gly116Asp substitutions, those changes were added to mRedB-595 to created mRedC-595.

We then screened for the best combination of these substitutions and identified E160D and S162N as the best combination, i.e. better than Asp115Gly/Gly116Asp. Subsequent random and targeted mutagenesis added the substitutions N6S, Q13R, H17Y, S96T, N98T, D128K, and D176N. H17Y is a reversion to the DsRed.M1 amino acid. The N98T substitution increases photostability. D128R and D128H also increase solubility.

The substitution Q64H was identified previously in a screen for increased photostability. The Q64H substitution on its own had no effect but conferred photostability in combination with F99Y. In the mRed-595 context, Q64H alone increases both solubility and photostability. Further, the F99Y substitution is detrimental to solubility and has no effect on photostability. However, Q64H does not confer added photostability in mRed(sol)-595 or mRed(sol)-560 (below) and the combined effect of Q64H and F99Y in these variants is unknown, but may confer photostability since F99 is close to residues S96 and N98 which have been mutated.

Figure 14:
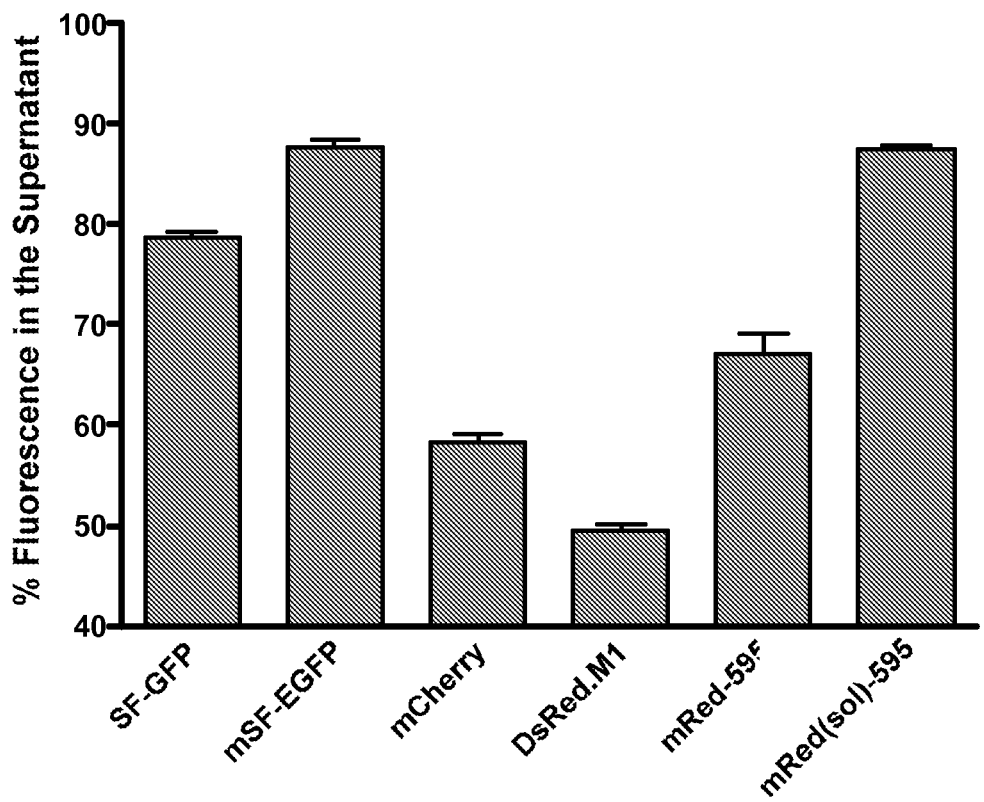
FIG. 14 is a bar graph showing the results of the monomeric protein aggregation assays with the mRed(sol)-595 variant.

The final variant is called mRed(sol)-595 and is as soluble as mSF-GFP in the aggregation assay when fused to the p53 tetramerization domain. mRed(sol)-595 contains the following substitutions relative to mRed-595: N6S, E10P, Q13R, I29V, W58Y, S96T, N98T, G115D, D116G, D128K, E160D, S162N, E168K, D176N, and Q188K. See Table 10. As shown in FIG. 14, mRed(sol)-595 is about as soluble in the p53 aggregation assay as SF-GFP. mRed(sol)-595 is now undergoing in vivo testing to evaluate its function as a fusion tag on "difficult" proteins in both yeast and mammalian cells.

TABLE 9

Aggregation reducing substitutions in mRed variants

| Residue | mRed-595 | mRedB-595 | mRedX-595 |
|---|---|---|---|
| 2 | Asp$^{GAC}$ | Asp$^{GAT}$ | Asp$^{GAT}$ |
| 3 | Asn$^{AAC}$ | Ser$^{AGC}$ | Ser$^{AGC}$ |
| 4 | Thr$^{ACC}$ | Thr$^{ACT}$ | Thr$^{ACT}$ |
| 10 | Glu | Pro | Pro |
| 17 | Tyr | His | His |
| 29 | Ile | Val | Val |
| 58 | Trp | Tyr | Tyr |
| 85 | Leu | Leu | Gln? |
| 115 | Gly | Asp | Gly? |
| 116 | Asp | Gly | Asp? |
| 128 | Asn | Asp | Asn? |
| 160 | Glu | Glu | Asp? |
| 162 | Ser | Ser | Asn? |
| 168 | Glu | Lys | Lys |
| 188 | Gln | Lys | Lys |
| 198 | Lys | Lys | Glu? |

The amino acids present at potentially substituted positions are listed for mRed-595, mRedB-595, and mRedX-595. mRedX-595 is the theoretical best variant after combination of all the site-directed aggregation-reducing substitutions. Superscripts indicate the codon used for residues 2-4. Undecided substitutions are indicated with a "?". Substitutions relative to mRed-595 are highlighted in bold.

TABLE 10

Substitutions relative to DsRed.M1

| Position | DsRed.M1 | mRed-580 | mRed-595 | mRed(sol)-595 | mRed(sol)-560 |
|---|---|---|---|---|---|
| 2 | Asp | Asp (GAT) | Asp (GAT) | Asp (GAT) | Asp (GAT) |
| 3 | Asn | Ser (AGC) | Ser (AGC) | Ser (AGC) | Ser (AGC) |
| 4 | Thr | Thr (ACT) | Thr (ACT) | Thr (ACT) | Thr (ACT) |
| 6 | Asp | Asn | Asn | Ser | Ser |
| 10 | Glu | Glu | Glu | Pro | Pro |
| 13 | Gln | Gln | Gln | Arg | Arg |
| 17 | Arg | Tyr | Tyr | Tyr | Tyr |

TABLE 10-continued

| | | | | | |
|---|---|---|---|---|---|
| 29 | Ile | Ile | Ile | Val | Val |
| 44 | Ala | Ala | Val | Val | Val |
| 58 | Trp | Trp | Trp | Tyr | Tyr |
| 64 | Gln | Gln | Gln | His? | His? |
| 66 | Gln | Met | Met | Met | Thr |
| 73 | Val | Val | Val | Val | Ser |
| 75 | His | His | His | His | Cys |
| 83 | Met | Leu | Phe | Phe | Phe |
| 96 | Ser | Ser | Ser | Thr | Thr |
| 98 | Asn | Asn | Asn | Thr | Thr |
| 99 | Phe | Phe | Phe | Tyr? | Tyr? |
| 115 | Asp | Gly | Gly | Asp | Asp |
| 116 | Gly | Asp | Asp | Gly | Gly |
| 121 | Lys | His | His | His | His |
| 124 | Phe | Val | Phe | Phe | Phe |
| 128 | Asp | Asp | Asp | Lys | Lys |
| 141 | Ala | Leu | Leu | Leu | Leu |
| 150 | Leu | Met | Met | Met | Met |
| 160 | Glu | Glu | Glu | Asp | Asp |
| 162 | Ser | Ser | Ser | Asn | Asn |
| 163 | His | Met | Met | Met | Met |
| 168 | Lys | Glu | Glu | Lys | Lys |
| 169 | Asp | Gly | Gly | Gly | Gly |
| 174 | Thr | Asn | Asn | Asn | Asn |
| 176 | Asp | Asp | Asp | Asn | Asn |
| 177 | Phe | Val | Val | Val | Val |
| 182 | Lys | Lys | Lys | Lys | Arg |
| 188 | Gln | Gln | Gln | | Lys |
| 197 | Ser | Ile | Ile | Ile | Ile |
| 203 | Asn | Ser | Ser | Ser | Ser |
| 213 | Gln | Leu | Gln | Gln | Gln |
| 217 | Ala | Ala | Ser | Ser | Ser |

Each variant in the table except mRed-595 is derived from the one to its left. mRed-595 is derived from DsRed.M1. A substitution relative to the parental variant is indicated by shading.

Example 17

Blue-Shifting mRed(Sol)-595 to Create mRed(Sol)-560

Figure 15:
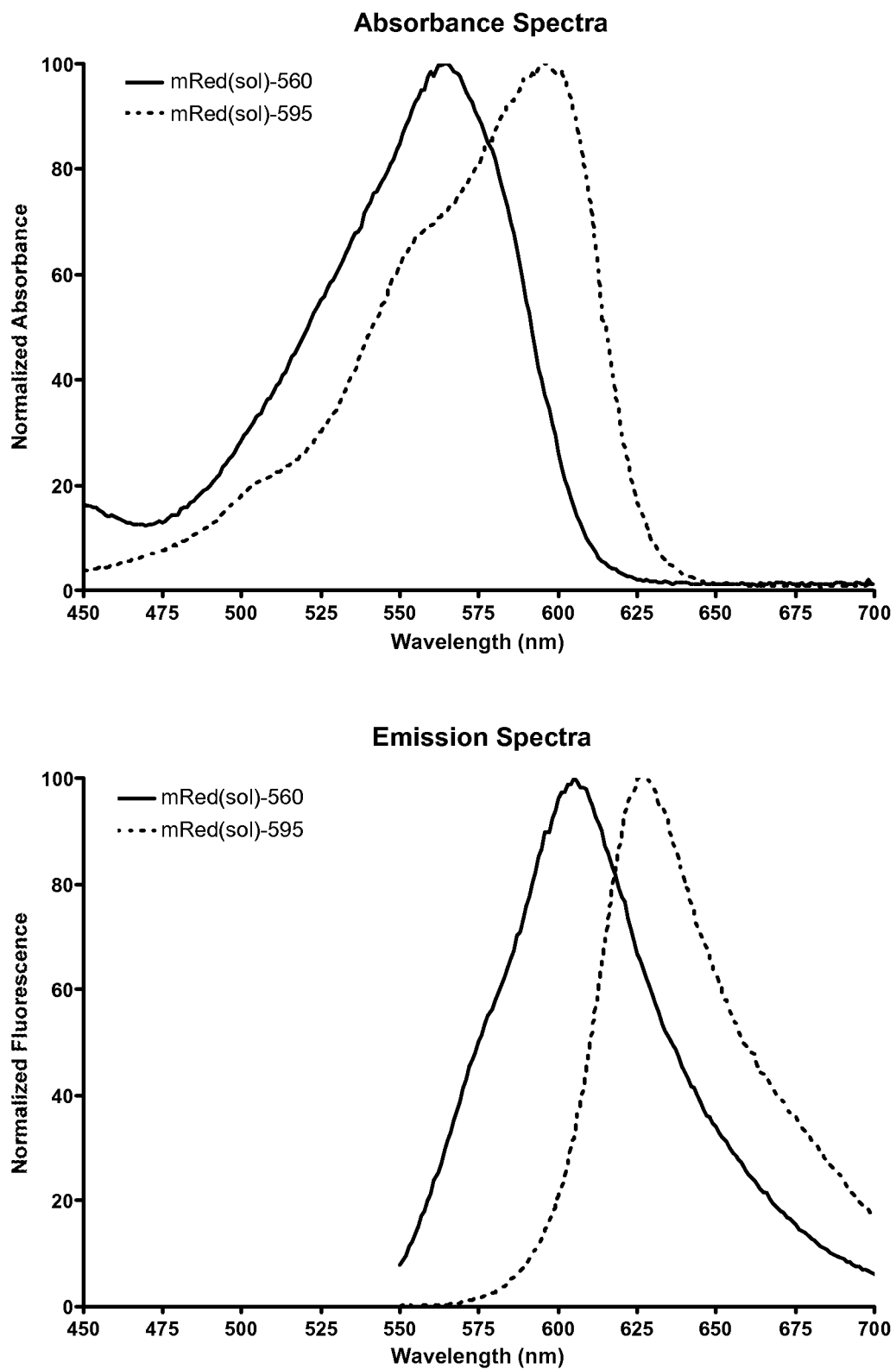
FIG. 15 is a set of graphs showing the absorbance and emission spectra of mRed(sol)-560 and mRed(sol)-595.

An extremely soluble red monomer with excitation and emission spectra similar to WT DsRed was also a goal. We decided that blue shifting an optimized far-red variant (i.e. mRed(sol)-595) was the best strategy. A series of WT-like red variants were unintentionally identified during random mutagenesis of mRed-595 for solubility enhancement. These variants all contained the M66T substitution. We then used random and directed mutagenesis of mRed(sol)-595+M66T to create a bright red soluble monomer. The resulting variant called mRed(sol)-560 has WT-like excitation and emission spectra as well as the enhanced solubility of mRed(sol)-595. mRed(sol)-560 contains the following substitutions relative to mRed(sol)-595: M66T, V73S, and K182R. Table 10. As described above V73 can also be substituted with Ala, Ile, or Thr, and H75 may be substituted with Arg or Cys and likely Lys. The Arg substitution at position 75 greatly increases brightness but adds a component of green fluorescence. Blue-shifting a red-shifted chromophore by altering the chromophore structure represents a novel approach to generating WT-like spectral properties. In this way we were able to take advantage of the optimal biochemical properties of mRed (sol)-595 while regaining the spectral position of WT-DsRed as shown in FIG. 15. The mRed-580 substitutions relative to mRed-595, namely V44A, F83L, F124V, Q213L, and S217A, might also be added to mRed(sol)-595 to create a variant that would be called mRed(sol)-580.

We claim:

1. An isolated polynucleotide encoding a variant polypeptide of SEQ ID NO:1, the variant polypeptide having fluorescence, having reduced aggregation relative to SEQ ID NO:1, having a sequence identity of 90% or more with SEQ ID NO:1 or SEQ ID NO:5, and comprising a proline residue at position 10 of SEQ ID NO:1 or SEQ ID NO:5.

2. The polynucleotide of claim 1, wherein the variant polypeptide comprises an aspartate residue at position 2 of SEQ ID NO:1 or SEQ ID NO:5 and a threonine residue at position 4 of SEQ ID NO:1 or SEQ ID NO:5.

3. The polynucleotide of claim 1, wherein the variant polypeptide comprises at least one amino acid selected from the group consisting of a methionine residue at position 66, a threonine or alanine residue at position 73, a lysine, cysteine, or arginine residue at position 75, a cysteine residue at position 175 and an alanine residue at position 219, relative to SEQ ID NO:1 or SEQ ID NO:5.

4. The polynucleotide of claim 1, wherein the variant polypeptide further comprises at least one amino acid selected from the group consisting of a lysine residue at position 36, a glutamine residue at position 47, a histidine residue at position 121, a leucine residue at position 141, a glycine residue at position 169, a valine residue at position 210, and a glutamine residue at position 225, relative to SEQ ID NO:1 or SEQ ID NO:5.

5. The polynucleotide of claim 1, wherein the variant polypeptide further comprises at least one amino acid selected from the group consisting of a threonine residue at position 117, a proline residue at position 145, and an alanine residue at position 217, relative to SEQ ID NO:1 or SEQ ID NO:5.

6. The isolated polynucleotide of claim 1, wherein the polynucleotide further encodes a polypeptide of interest linked to the variant polypeptide, the polypeptide of interest and the variant polypeptide being expressed as a fusion protein.

7. A cell comprising the sequence of claim 1.

8. A construct comprising the polynucleotide of claim 1 operably connected to a promoter.

9. A vector comprising the construct of claim 8.

10. A method of obtaining expression of a variant polypeptide of SEQ ID NO:1 comprising introducing the vector of claim 9 into a host cell under conditions that permit expression of the variant polypeptide.

11. The method of claim 10, wherein the polynucleotide further encodes a polypeptide of interest linked to the variant polypeptide, the polypeptide of interest and the variant polypeptide being expressed as a fusion protein.

12. The method of claim 10, further comprising evaluating the expression of the variant polypeptide by detecting red fluorescence.

13. The method of claim 12, further comprising monitoring temporal or spatial changes in red fluorescence.

14. The polynucleotide of claim 4, wherein the variant polypeptide comprises a glycine residue at position 169, relative to SEQ ID NO:1 or SEQ ID NO:5.

15. The polynucleotide of claim 1, wherein the variant polypeptide comprises a lysine residue at position 188, relative to SEQ ID NO:1 or SEQ ID NO:5.

16. The polynucleotide of claim 15, wherein the variant polypeptide further comprises a glycine residue at position 169, relative to SEQ ID NO:1 or SEQ ID NO:5.

17. The isolated polynucleotide of claim 16, wherein the polynucleotide further encodes a polypeptide of interest linked to the variant polypeptide, the polypeptide of interest and the variant polypeptide being expressed as a fusion protein.

18. A cell comprising the polynucleotide of claim 17.

19. A construct comprising the polynucleotide of claim 17 operably connected to a promoter.

20. A vector comprising the construct of claim 19.

21. A method of obtaining expression of a variant polypeptide of SEQ ID NO:1 comprising introducing the vector of claim 19 into a host cell under conditions that permit expression of the variant polypeptide.

* * * * *

SEQUENCE LISTING

```
<160> NUMBER OF SEQ ID NOS: 31

<210> SEQ ID NO 1
<211> LENGTH: 225
<212> TYPE: PRT
<213> ORGANISM: Discosoma

<400> SEQUENCE: 1

Met Arg Ser Ser Lys Asn Val Ile Lys Glu Phe Met Arg Phe Lys Val
1               5                   10                  15
```

```
Arg Met Glu Gly Thr Val Asn Gly His Glu Phe Glu Ile Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 2
<211> LENGTH: 225
<212> TYPE: PRT
<213> ORGANISM: Artificial Sequence
<220> FEATURE:
<223> OTHER INFORMATION: Chemically synthesized protein: DsRed.T1

<400> SEQUENCE: 2

Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
```

```
                145                 150                 155                 160
Ile His Lys Ala Leu Lys Leu Lys Asp Gly Gly His Tyr Leu Val Glu
                    165                 170                 175

Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
                    195                 200                 205

Thr Ile Val Glu Gln Tyr Glu Arg Ala Glu Gly Arg His His Leu Phe
        210                 215                 220

Leu
225

<210> SEQ ID NO 3
<211> LENGTH: 225
<212> TYPE: PRT
<213> ORGANISM: Artificial Sequence
<220> FEATURE:
<223> OTHER INFORMATION: Chemically synthesized protein: DsRed.T3

<400> SEQUENCE: 3

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
                20                  25                  30

Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
                100                 105                 110

Leu Gln Asp Gly Cys Phe Ile Tyr Lys Val Lys Phe Ile Gly Val Asn
            115                 120                 125

Phe Pro Ser Asp Gly Pro Val Met Gln Lys Lys Thr Met Gly Trp Glu
    130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Thr Glu Gly Arg His His Leu Phe
    210                 215                 220

Leu
225

<210> SEQ ID NO 4
<211> LENGTH: 225
<212> TYPE: PRT
<213> ORGANISM: Artificial Sequence
<220> FEATURE:
<223> OTHER INFORMATION: Chemically synthesized protein: DsRed-Max
```

<400> SEQUENCE: 4

```
Met Asp Ser Thr Glu Asn Val Ile Lys Pro Phe Met Arg Phe Lys Val
1               5                   10                  15

His Met Glu Gly Ser Val Asn Gly His Glu Phe Glu Ile Glu Gly Glu
            20                  25                  30

Gly Glu Gly Lys Pro Tyr Glu Gly Thr Gln Thr Ala Lys Leu Gln Val
        35                  40                  45

Thr Lys Gly Gly Pro Leu Pro Phe Ala Trp Asp Ile Leu Ser Pro Gln
    50                  55                  60

Phe Met Tyr Gly Ser Lys Val Tyr Thr Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Thr Phe Ile Tyr His Val Lys Phe Ile Gly Val Asn
        115                 120                 125

Phe Pro Ser Asp Gly Pro Val Met Gln Lys Lys Thr Leu Gly Trp Glu
130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Gly Gly His Tyr Leu Cys Glu
                165                 170                 175

Phe Lys Ser Ile Tyr Met Ala Lys Lys Pro Val Lys Leu Pro Gly Tyr
            180                 185                 190

Tyr Tyr Val Asp Ser Lys Leu Asp Ile Thr Ser His Asn Glu Asp Tyr
        195                 200                 205

Thr Val Val Glu Gln Tyr Glu Arg Thr Glu Ala Arg His His Leu Phe
    210                 215                 220

Gln
225
```

<210> SEQ ID NO 5
<211> LENGTH: 225
<212> TYPE: PRT
<213> ORGANISM: Artificial Sequence
<220> FEATURE:
<223> OTHER INFORMATION: Chemically synthesized protein: DsRed-Express2

<400> SEQUENCE: 5

```
Met Asp Ser Thr Glu Asn Val Ile Lys Pro Phe Met Arg Phe Lys Val
1               5                   10                  15

His Met Glu Gly Ser Val Asn Gly His Glu Phe Glu Ile Glu Gly Glu
            20                  25                  30

Gly Glu Gly Lys Pro Tyr Glu Gly Thr Gln Thr Ala Lys Leu Gln Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Thr Phe Ile Tyr His Val Lys Phe Ile Gly Val Asn
        115                 120                 125
```

Phe Pro Ser Asp Gly Pro Val Met Gln Lys Thr Leu Gly Trp Glu
            130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Gly Gly His Tyr Leu Val Glu
                165                 170                 175

Phe Lys Ser Ile Tyr Met Ala Lys Lys Pro Val Lys Leu Pro Gly Tyr
                180                 185                 190

Tyr Tyr Val Asp Ser Lys Leu Asp Ile Thr Ser His Asn Glu Asp Tyr
        195                 200                 205

Thr Val Val Glu Gln Tyr Glu Arg Ala Glu Ala Arg His His Leu Phe
    210                 215                 220

Gln
225

<210> SEQ ID NO 6
<211> LENGTH: 225
<212> TYPE: PRT
<213> ORGANISM: Artificial Sequence
<220> FEATURE:
<223> OTHER INFORMATION: Chemically synthesized protein: DsRed.M1

<400> SEQUENCE: 6

Met Asp Asn Thr Glu Asp Val Ile Lys Glu Phe Met Gln Phe Lys Val
1               5                   10                  15

Arg Met Glu Gly Ser Val Asn Gly His Tyr Phe Glu Ile Glu Gly Glu
            20                  25                  30

Gly Glu Gly Lys Pro Tyr Glu Gly Thr Gln Thr Ala Lys Leu Gln Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Met Lys Leu Ser Phe Pro Glu Gly Phe Thr Trp Glu Arg Ser
                85                  90                  95

Met Asn Phe Glu Asp Gly Gly Val Val Glu Val Gln Gln Asp Ser Ser
            100                 105                 110

Leu Gln Asp Gly Thr Phe Ile Tyr Lys Val Lys Phe Lys Gly Val Asn
        115                 120                 125

Phe Pro Ala Asp Gly Pro Val Met Gln Lys Lys Thr Ala Gly Trp Glu
    130                 135                 140

Pro Ser Thr Glu Lys Leu Tyr Pro Gln Asp Gly Val Leu Lys Gly Glu
145                 150                 155                 160

Ile Ser His Ala Leu Lys Leu Lys Asp Gly Gly His Tyr Thr Cys Asp
                165                 170                 175

Phe Lys Thr Val Tyr Lys Ala Lys Lys Pro Val Gln Leu Pro Gly Asn
                180                 185                 190

His Tyr Val Asp Ser Lys Leu Asp Ile Thr Asn His Asn Glu Asp Tyr
        195                 200                 205

Thr Val Val Glu Gln Tyr Glu His Ala Glu Ala Arg His Ser Gly Ser
    210                 215                 220

Gln
225

<210> SEQ ID NO 7
<211> LENGTH: 225

```
<212> TYPE: PRT
<213> ORGANISM: Artificial Sequence
<220> FEATURE:
<223> OTHER INFORMATION: Chemically synthesized protein: mRed-555

<400> SEQUENCE: 7

Met Asp Asn Thr Glu Asn Val Ile Lys Glu Phe Met Gln Phe Lys Val
1               5                   10                  15

Tyr Met Glu Gly Ser Val Asn Gly His Tyr Phe Glu Ile Glu Gly Glu
            20                  25                  30

Gly Glu Gly Lys Pro Tyr Glu Gly Thr Gln Thr Ala Lys Leu Gln Val
        35                  40                  45

Thr Lys Gly Gly Pro Leu Pro Phe Ala Trp Asp Ile Leu Ser Pro Gln
    50                  55                  60

Phe Met Tyr Gly Ser Lys Ala Tyr Val Lys His Pro Ala Asp Ile Pro
65                  70                  75                  80

Asp Tyr Leu Lys Leu Ser Phe Pro Glu Gly Phe Thr Trp Glu Arg Ser
                85                  90                  95

Met Asn Phe Glu Asp Gly Gly Val Val Glu Val Gln Gln Asp Ser Ser
            100                 105                 110

Leu Gln Gly Asp Thr Phe Ile Tyr His Val Lys Phe Lys Gly Val Asn
        115                 120                 125

Phe Pro Ala Asp Gly Pro Val Met Gln Lys Lys Thr Leu Gly Trp Glu
130                 135                 140

Pro Ser Thr Glu Lys Leu Tyr Pro Gln Asp Gly Val Leu Lys Gly Glu
145                 150                 155                 160

Ile Ser His Ala Leu Lys Leu Glu Gly Gly Gly His Tyr Asn Cys Asp
                165                 170                 175

Phe Lys Thr Val Tyr Lys Ala Lys Lys Pro Val Gln Leu Pro Gly Asn
            180                 185                 190

His Tyr Val Asp Ser Lys Leu Asp Ile Thr Ser His Asn Glu Asp Tyr
        195                 200                 205

Thr Val Val Glu Gln Tyr Glu His Ser Glu Ala Arg His Ser Gly Ser
    210                 215                 220

Gln
225

<210> SEQ ID NO 8
<211> LENGTH: 225
<212> TYPE: PRT
<213> ORGANISM: Artificial Sequence
<220> FEATURE:
<223> OTHER INFORMATION: Chemically synthesized protein: mRed-580

<400> SEQUENCE: 8

Met Asp Asn Thr Glu Asn Val Ile Lys Glu Phe Met Gln Phe Lys Val
1               5                   10                  15

Tyr Met Glu Gly Ser Val Asn Gly His Tyr Phe Glu Ile Glu Gly Glu
            20                  25                  30

Gly Glu Gly Lys Pro Tyr Glu Gly Thr Gln Thr Ala Lys Leu Gln Val
        35                  40                  45

Thr Lys Gly Gly Pro Leu Pro Phe Ala Trp Asp Ile Leu Ser Pro Gln
    50                  55                  60

Phe Met Tyr Gly Ser Lys Ala Tyr Val Lys His Pro Ala Asp Ile Pro
65                  70                  75                  80

Asp Tyr Leu Lys Leu Ser Phe Pro Glu Gly Phe Thr Trp Glu Arg Ser
                85                  90                  95
```

```
Met Asn Phe Glu Asp Gly Gly Val Val Glu Val Gln Gln Asp Ser Ser
            100                 105                 110
Leu Gln Gly Asp Thr Phe Ile Tyr His Val Lys Val Lys Gly Val Asn
            115                 120                 125
Phe Pro Ala Asp Gly Pro Val Met Gln Lys Lys Thr Leu Gly Trp Glu
130                 135                 140
Pro Ser Thr Glu Lys Met Tyr Pro Gln Asp Gly Val Leu Lys Gly Glu
145                 150                 155                 160
Ile Ser Met Ala Leu Lys Leu Glu Gly Gly Gly His Tyr Asn Cys Asp
                165                 170                 175
Val Lys Thr Val Tyr Lys Ala Lys Lys Pro Val Gln Leu Pro Gly Asn
            180                 185                 190
His Tyr Val Asp Ile Lys Leu Asp Ile Thr Ser His Asn Glu Asp Tyr
            195                 200                 205
Thr Val Val Glu Leu Tyr Glu His Ala Glu Ala Arg His Ser Gly Ser
            210                 215                 220
Gln
225

<210> SEQ ID NO 9
<211> LENGTH: 225
<212> TYPE: PRT
<213> ORGANISM: Artificial Sequence
<220> FEATURE:
<223> OTHER INFORMATION: Chemically synthesized protein: mRed-595

<400> SEQUENCE: 9

Met Asp Asn Thr Glu Asn Val Ile Lys Glu Phe Met Gln Phe Lys Val
1               5                   10                  15
Tyr Met Glu Gly Ser Val Asn Gly His Tyr Phe Glu Ile Glu Gly Glu
            20                  25                  30
Gly Glu Gly Lys Pro Tyr Glu Gly Thr Gln Thr Val Lys Leu Gln Val
            35                  40                  45
Thr Lys Gly Gly Pro Leu Pro Phe Ala Trp Asp Ile Leu Ser Pro Gln
        50                  55                  60
Phe Met Tyr Gly Ser Lys Ala Tyr Val Lys His Pro Ala Asp Ile Pro
65                  70                  75                  80
Asp Tyr Phe Lys Leu Ser Phe Pro Glu Gly Phe Thr Trp Glu Arg Ser
                85                  90                  95
Met Asn Phe Glu Asp Gly Gly Val Val Glu Val Gln Gln Asp Ser Ser
            100                 105                 110
Leu Gln Gly Asp Thr Phe Ile Tyr His Val Lys Phe Lys Gly Val Asn
            115                 120                 125
Phe Pro Ala Asp Gly Pro Val Met Gln Lys Lys Thr Leu Gly Trp Glu
130                 135                 140
Pro Ser Thr Glu Lys Met Tyr Pro Gln Asp Gly Val Leu Lys Gly Glu
145                 150                 155                 160
Ile Ser Met Ala Leu Lys Leu Glu Gly Gly Gly His Tyr Asn Cys Asp
                165                 170                 175
Val Lys Thr Val Tyr Lys Ala Lys Lys Pro Val Gln Leu Pro Gly Asn
            180                 185                 190
His Tyr Val Asp Ile Lys Leu Asp Ile Thr Ser His Asn Glu Asp Tyr
            195                 200                 205
Thr Val Val Glu Gln Tyr Glu His Ser Glu Ala Arg His Ser Gly Ser
            210                 215                 220
Gln
```

<210> SEQ ID NO 10
<211> LENGTH: 225
<212> TYPE: PRT
<213> ORGANISM: Artificial Sequence
<220> FEATURE:
<223> OTHER INFORMATION: Chemically synthesized protein: mRedB-595

<400> SEQUENCE: 10

```
Met Asp Ser Thr Glu Asn Val Ile Lys Pro Phe Met Arg Phe Lys Val
1               5                   10                  15

His Met Glu Gly Ser Val Asn Gly His Tyr Phe Glu Val Glu Gly Glu
            20                  25                  30

Gly Glu Gly Lys Pro Tyr Glu Gly Thr Gln Thr Val Lys Leu Gln Val
        35                  40                  45

Thr Lys Gly Gly Pro Leu Pro Phe Ala Tyr Asp Ile Leu Ser Pro Gln
    50                  55                  60

Phe Met Tyr Gly Ser Lys Ala Tyr Val Lys His Pro Ala Asp Ile Pro
65                  70                  75                  80

Asp Tyr Phe Lys Leu Ser Phe Pro Glu Gly Phe Thr Trp Glu Arg Ser
                85                  90                  95

Met Asn Phe Glu Asp Gly Gly Val Val Glu Val Gln Gln Asp Ser Ser
            100                 105                 110

Leu Gln Asp Gly Thr Phe Ile Tyr His Val Lys Phe Lys Gly Val Asp
        115                 120                 125

Phe Pro Ala Asp Gly Pro Val Met Gln Lys Lys Thr Leu Gly Trp Glu
    130                 135                 140

Pro Ser Thr Glu Lys Met Tyr Pro Gln Asp Gly Val Leu Lys Gly Glu
145                 150                 155                 160

Ile Ser Met Ala Leu Lys Leu Lys Gly Gly Gly His Tyr Asn Cys Asp
                165                 170                 175

Val Lys Thr Val Tyr Lys Ala Lys Lys Pro Val Lys Leu Pro Gly Asn
            180                 185                 190

His Tyr Val Asp Ile Lys Leu Asp Ile Thr Ser His Asn Glu Asp Tyr
        195                 200                 205

Thr Val Val Glu Gln Tyr Glu His Ser Glu Ala Arg His Ser Gly Ser
    210                 215                 220

Gln
225
```

<210> SEQ ID NO 11
<211> LENGTH: 678
<212> TYPE: DNA
<213> ORGANISM: Discosoma

<400> SEQUENCE: 11

```
atgaggtctt ccaagaatgt tatcaaggag ttcatgaggt ttaaggttcg catggaagga      60
acggtcaatg ggcacgagtt tgaaatagaa ggcgaaggag aggggaggcc atacgaaggc     120
cacaataccg taaagcttaa ggtaaccaag ggggaccctt tgccatttgc ttgggatatt     180
ttgtcaccac aatttcagta tggaagcaag gtatatgtca agcaccctgc cgacatacca     240
gactataaaa gctgtcatt tcctgaagga tttaaatggg aaagggtcat gaactttgaa     300
gacggtggcg tcgttactgt aacccaggat tccagtttgc aggatggctg tttcatctac     360
aaggtcaagt tcattggcgt gaactttcct tccgatggac ctgttatgca aaagaagaca     420
atgggctggg aagccagcac tgagcgtttg tatcctcgtg atggcgtgtt gaaaggagag     480
```

```
attcataagg ctctgaagct gaaagacggt ggtcattacc tagttgaatt caaaagtatt    540
tacatggcaa agaagcctgt gcagctacca gggtactact atgttgactc caaactggat    600
ataacaagcc acaacgaaga ctatacaatc gttgagcagt atgaaagaac cgagggacgc    660
caccatctgt tcctttaa                                                  678
```

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 12

```
catggaytcn acngaraacg t                                              21
```

<210> SEQ ID NO 13
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 13

```
tytcngtnga rtc                                                       13
```

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: n is a, c, g, or t

<400> SEQUENCE: 14

```
catggayagy acngaraacg t                                              21
```

<210> SEQ ID NO 15
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t -continued

```
<400> SEQUENCE: 15
tytcngtnga rtc                                                         13

<210> SEQ ID NO 16
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 16
gatagcactg ag                                                          12

<210> SEQ ID NO 17
<211> LENGTH: 226
<212> TYPE: PRT
<213> ORGANISM: Artificial Sequence
<220> FEATURE:
<223> OTHER INFORMATION: Chemically synthesized protein: Plum

<400> SEQUENCE: 17

Met Val Ser Lys Gly Glu Glu Val Ile Lys Glu Phe Met Arg Phe Lys
 1               5                  10                  15

Glu His Met Glu Gly Ser Val Asn Gly His Glu Phe Glu Ile Glu Gly
            20                  25                  30

Glu Gly Glu Gly Arg Pro Tyr Glu Gly Thr Gln Thr Ala Arg Leu Lys
        35                  40                  45

Val Thr Lys Gly Gly Pro Leu Pro Phe Ala Trp Asp Ile Leu Ser Pro
    50                  55                  60

Gln Ile Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Val Arg Gly Thr
        115                 120                 125

Asn Phe Pro Ser Asp Gly Pro Val Met Gln Lys Lys Thr Met Gly Trp
    130                 135                 140

Glu Ala Ser Ser Glu Arg Met Tyr Pro Glu Asp Gly Ala Leu Lys Gly
145                 150                 155                 160

Glu Met Lys Met Arg Leu Arg Leu Lys Asp Gly His Tyr Asp Ala
                165                 170                 175

Glu Val Lys Thr Thr Tyr Met Ala Lys Lys Pro Val Gln Leu Pro Gly
            180                 185                 190

Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
    210                 215                 220

Gly Ala
225

<210> SEQ ID NO 18
<211> LENGTH: 226
<212> TYPE: PRT
<213> ORGANISM: Artificial Sequence
<220> FEATURE:
<223> OTHER INFORMATION: Chemically synthesized protein: rasberry
```

-continued

<400> SEQUENCE: 18

Met Val Ser Lys Gly Glu Glu Val Ile Lys Glu Phe Met Arg Phe Lys
1               5                   10                  15

Val Arg Met Glu Gly Ser Val Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
50                  55                  60

Gln Cys Met Tyr Gly Ser Lys Gly Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Leu Arg Gly Thr
        115                 120                 125

Asn Phe Pro Ser Asp Gly Pro Val Met Gln Lys Lys Thr Met Gly Trp
130                 135                 140

Glu Ala Ser Ser Glu Arg Met Tyr Pro Glu Asp Gly Ala Leu Lys Gly
145                 150                 155                 160

Glu Met Lys Met Arg Leu Lys Leu Lys Asp Gly Gly His Tyr Asp Ala
                165                 170                 175

Glu Val Lys Thr Thr Tyr Met Ala Lys Lys Pro Val Gln Leu Pro Gly
            180                 185                 190

Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
210                 215                 220

Gly Ala
225

<210> SEQ ID NO 19
<211> LENGTH: 225
<212> TYPE: PRT
<213> ORGANISM: Artificial Sequence
<220> FEATURE:
<223> OTHER INFORMATION: Chemically synthesized protein: mHoneyDew

<400> SEQUENCE: 19

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Met Trp Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

```
Phe Pro Ser Asp Gly Pro Val Met Gln Lys Lys Thr Met Gly Trp Ala
        130                 135                 140

Ala Thr Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Ile Asp Gly Lys Leu Asp Ile Thr Ser His Asn Glu Asp Tyr
            195                 200                 205

Thr Ile Val Glu Gln Tyr Glu Arg Ala Glu Gly Arg His Ser Thr Gly
        210                 215                 220

Ala
225

<210> SEQ ID NO 20
<211> LENGTH: 225
<212> TYPE: PRT
<213> ORGANISM: Artificial Sequence
<220> FEATURE:
<223> OTHER INFORMATION: Chemically synthesized protein: mtangerine

<400> SEQUENCE: 20

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Cys Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Ser Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
            195                 200                 205

Thr Ile Val Glu Leu Tyr Glu Arg Ala Glu Gly Arg His Ser Thr Gly
        210                 215                 220

Ala
225

<210> SEQ ID NO 21
<211> LENGTH: 234
```

```
<212> TYPE: PRT
<213> ORGANISM: Artificial Sequence
<220> FEATURE:
<223> OTHER INFORMATION: Chemically synthesized protein: dTomato

<400> SEQUENCE: 21

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Tyr Gly Met Asp Glu Leu Tyr Lys
225                 230

<210> SEQ ID NO 22
<211> LENGTH: 236
<212> TYPE: PRT
<213> ORGANISM: Artificial Sequence
<220> FEATURE:
<223> OTHER INFORMATION: Chemically synthesized protein: mBanana

<400> SEQUENCE: 22

Met Val Ser Lys Gly Glu Glu Asn Asn Met Ala Val Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Cys Tyr Gly Ser Lys Ala Tyr Val Lys His
65                  70                  75                  80

Pro Thr Gly Ile Pro Asp Tyr Phe Lys Leu Ser Phe Pro Glu Gly Phe
                85                  90                  95
```

```
Lys Trp Glu Arg Val Met Asn Phe Glu Asp Gly Gly Val Val Thr Val
            100                 105                 110

Ala Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Ser Ala Glu Thr Lys Thr Thr Tyr Lys Ala Lys Lys Pro Val
            180                 185                 190

Gln Leu Pro Gly Ala Tyr Ile Ala Gly Glu Lys Ile Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 23
<211> LENGTH: 236
<212> TYPE: PRT
<213> ORGANISM: Artificial Sequence
<220> FEATURE:
<223> OTHER INFORMATION: Chemically synthesized protein: strawberry

<400> SEQUENCE: 23

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Thr Pro Asn Phe Thr Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
```

225                 230                 235

<210> SEQ ID NO 24
<211> LENGTH: 236
<212> TYPE: PRT
<213> ORGANISM: Artificial Sequence
<220> FEATURE:
<223> OTHER INFORMATION: Chemically synthesized protein: mOrange

<400> SEQUENCE: 24

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 25
<211> LENGTH: 236
<212> TYPE: PRT
<213> ORGANISM: Artificial Sequence
<220> FEATURE:
<223> OTHER INFORMATION: Chemically synthesized protein: mCherry

<400> SEQUENCE: 25

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His

```
                65                  70                  75                  80
Pro Ala Asp Ile Pro Asp Tyr Leu Lys Leu Ser Phe Pro Glu Gly Phe
                    85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Gln Lys Lys
            130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
        210                 215                 220

Arg His Ser Thr Gly Gly Met Asp Glu Leu Tyr Lys
225                 230                 235

<210> SEQ ID NO 26
<211> LENGTH: 225
<212> TYPE: PRT
<213> ORGANISM: Artificial Sequence
<220> FEATURE:
<223> OTHER INFORMATION: Chemically synthesized protein: mRFP1

<400> SEQUENCE: 26

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
                20                  25                  30

Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
                100                 105                 110

Leu Gln Asp Gly Glu Phe Ile Tyr Lys Val Lys Leu Arg Gly Thr Asn
            115                 120                 125

Phe Pro Ser Asp Gly Pro Val Met Gln Lys Lys Thr Met Gly Trp Glu
        130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
                180                 185                 190

Tyr Lys Thr Asp Ile Lys Leu Asp Ile Thr Ser His Asn Glu Asp Tyr
            195                 200                 205
```

```
Thr Ile Val Glu Gln Tyr Glu Arg Ala Glu Gly Arg His Ser Thr Gly
    210                 215                 220

Ala
225

<210> SEQ ID NO 27
<211> LENGTH: 225
<212> TYPE: PRT
<213> ORGANISM: Artificial Sequence
<220> FEATURE:
<223> OTHER INFORMATION: Chemically synthesized protein: mRFP1-1

<400> SEQUENCE: 27

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Met Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Ser Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 28
<211> LENGTH: 224
<212> TYPE: PRT
<213> ORGANISM: Artificial Sequence
<220> FEATURE:
<223> OTHER INFORMATION: Chemically synthesized protein: DsRed_Monomer

<400> SEQUENCE: 28

Asp Asn Thr Glu Asp Val Ile Lys Glu Phe Met Gln Phe Lys Val Arg
1               5                   10                  15

Met Glu Gly Ser Val Asn Gly His Tyr Phe Glu Ile Glu Gly Glu Gly
            20                  25                  30

Glu Gly Lys Pro Tyr Glu Gly Thr Gln Thr Ala Lys Leu Gln Val Thr
        35                  40                  45
```

```
Lys Gly Gly Pro Leu Pro Phe Ala Trp Asp Ile Leu Ser Pro Gln Phe
 50                  55                  60
Gln Tyr Gly Ser Lys Ala Tyr Val Lys His Pro Ala Asp Ile Pro Asp
 65                  70                  75                  80
Tyr Met Lys Leu Ser Phe Pro Glu Gly Phe Thr Trp Glu Arg Ser Met
                 85                  90                  95
Asn Phe Glu Asp Gly Val Val Glu Val Gln Gln Asp Ser Ser Leu
                100                 105                 110
Gln Asp Gly Thr Phe Ile Tyr Lys Val Lys Phe Lys Gly Val Asn Phe
            115                 120                 125
Pro Ala Asp Gly Pro Val Met Gln Lys Lys Thr Ala Gly Trp Glu Pro
130                 135                 140
Ser Thr Glu Lys Leu Tyr Pro Gln Asp Gly Val Leu Lys Gly Glu Ile
145                 150                 155                 160
Ser His Ala Leu Lys Leu Lys Asp Gly Gly His Tyr Thr Cys Asp Phe
                165                 170                 175
Lys Thr Val Tyr Lys Ala Lys Lys Pro Val Gln Leu Pro Gly Asn His
                180                 185                 190
Tyr Val Asp Ser Lys Leu Asp Ile Thr Asn His Asn Glu Asp Tyr Thr
            195                 200                 205
Val Val Glu Gln Tyr Glu His Ala Glu Ala Arg His Ser Gly Ser Gln
210                 215                 220

<210> SEQ ID NO 29
<211> LENGTH: 225
<212> TYPE: PRT
<213> ORGANISM: Artificial Sequence
<220> FEATURE:
<223> OTHER INFORMATION: Chemically synthesized protein: DsRedExpress

<400> SEQUENCE: 29

Met Ala Ser Ser Glu Asp Val Ile Lys Glu Phe Met Arg Phe Lys Val
 1               5                  10                  15
Arg Met Glu Gly Ser Val Asn Gly His Glu Phe Glu Ile Glu Gly Glu
                20                  25                  30
Gly Glu Gly Arg Pro Tyr Glu Gly Thr Gln Thr Ala Lys Leu Lys Val
            35                  40                  45
Thr Lys Gly Gly Pro Leu Pro Phe Ala Trp Asp Ile Leu Ser Pro Gln
 50                  55                  60
Phe Gln Tyr Gly Ser Lys Val Tyr Val Lys His Pro Ala Asp Ile Pro
 65                  70                  75                  80
Asp Tyr Lys Lys Leu Ser Phe Pro Glu Gly Phe Lys Trp Glu Arg Val
                 85                  90                  95
Met Asn Phe Glu Asp Gly Gly Val Val Thr Val Thr Gln Asp Ser Ser
                100                 105                 110
Leu Gln Asp Gly Ser Phe Ile Tyr Lys Val Lys Phe Ile Gly Val Asn
            115                 120                 125
Phe Pro Ser Asp Gly Pro Val Met Gln Lys Lys Thr Met Gly Trp Glu
130                 135                 140
Ala Ser Thr Glu Arg Leu Tyr Pro Arg Asp Gly Val Leu Lys Gly Glu
145                 150                 155                 160
Ile His Lys Ala Leu Lys Leu Lys Asp Gly Gly His Tyr Leu Val Glu
                165                 170                 175
Phe Lys Ser Ile Tyr Met Ala Lys Lys Pro Val Gln Leu Pro Gly Tyr
                180                 185                 190
```

```
Tyr Tyr Val Asp Ser Lys Leu Asp Ile Thr Ser His Asn Glu Asp Tyr
            195                 200                 205

Thr Ile Val Glu Gln Tyr Glu Arg Ala Glu Gly Arg His His Leu Phe
210                 215                 220

Leu
225

<210> SEQ ID NO 30
<211> LENGTH: 225
<212> TYPE: PRT
<213> ORGANISM: Artificial Sequence
<220> FEATURE:
<223> OTHER INFORMATION: Chemically synthesized protein: DsRed2

<400> SEQUENCE: 30

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
210                 215                 220

Leu
225

<210> SEQ ID NO 31
<211> LENGTH: 225
<212> TYPE: PRT
<213> ORGANISM: Artificial Sequence
<220> FEATURE:
<223> OTHER INFORMATION: Chemically synthesized protein: DsRed1-wt

<400> SEQUENCE: 31

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30
```

-continued

```
Gly Glu Gly Arg Pro Tyr Glu Gly His Asn Thr Val Lys Leu Lys Val
        35              40                  45

Thr Lys Gly Gly Pro Leu Pro Phe Ala Trp Asp Ile Leu Ser Pro Gln
    50              55                  60

Phe Gln Tyr Gly Ser Lys Val Tyr Val Lys His Pro Ala Asp Ile Pro
65              70                  75                      80

Asp Tyr Lys Lys Leu Ser Phe Pro Glu Gly Phe Lys Trp Glu Arg Val
            85                  90                  95

Met Asn Phe Glu Asp Gly Gly Val Val Thr Val Thr Gln Asp Ser Ser
            100             105                 110

Leu Gln Asp Gly Cys Phe Ile Tyr Lys Val Lys Phe Ile Gly Val Asn
        115             120                 125

Phe Pro Ser Asp Gly Pro Val Met Gln Lys Lys Thr Met Gly Trp Glu
    130             135                 140

Ala Ser Thr Glu Arg Leu Tyr Pro Arg Asp Gly Val Leu Lys Gly Glu
145             150             155                 160

Ile His Lys Ala Leu Lys Leu Lys Asp Gly Gly His Tyr Leu Val Glu
            165             170                 175

Phe Lys Ser Ile Tyr Met Ala Lys Lys Pro Val Gln Leu Pro Gly Tyr
            180             185                 190

Tyr Tyr Val Asp Ser Lys Leu Asp Ile Thr Ser His Asn Glu Asp Tyr
        195             200                 205

Thr Ile Val Glu Gln Tyr Glu Arg Thr Glu Gly Arg His His Leu Phe
        210             215                 220

Leu
225
```